US012806323B2

(12) United States Patent
Chiaki et al.

(10) Patent No.: US 12,806,323 B2
(45) Date of Patent: Nov. 24, 2026

(54) BLOOD PURIFICATION APPARATUS

(71) Applicant: Nikkiso Co., Ltd., Tokyo (JP)

(72) Inventors: Hikaru Chiaki, Shizuoka (JP); Takumi Homma, Shizuoka (JP); Yuya Menjoh, Shizuoka (JP); Kazuya Tsuji, Shizuoka (JP); Kunihiko Akita, Shizuoka (JP)

(73) Assignee: Nikkiso Co., Ltd., Tokyo (JP)

( * ) Notice: Subject to any disclaimer, the term of this patent is extended or adjusted under 35 U.S.C. 154(b) by 0 days.

(21) Appl. No.: 18/033,825

(22) PCT Filed: Jul. 27, 2021

(86) PCT No.: PCT/JP2021/027726
§ 371 (c)(1),
(2) Date: Apr. 26, 2023

(87) PCT Pub. No.: WO2022/102174
PCT Pub. Date: May 19, 2022

(65) Prior Publication Data

US 2023/0398277 A1 Dec. 14, 2023

(30) Foreign Application Priority Data

Nov. 13, 2020 (JP) ................................ 2020-189213

(51) Int. Cl.
*A61M 1/30* (2006.01)
*A61M 1/16* (2006.01)
(Continued)

(52) U.S. Cl.
CPC ............ *A61M 1/30* (2013.01); *A61M 1/1601* (2014.02); *A61M 1/1621* (2014.02);
(Continued)

(58) Field of Classification Search
None
See application file for complete search history.

(56) References Cited

U.S. PATENT DOCUMENTS

2005/0131332 A1* 6/2005 Kelly .............. A61M 1/362265 604/4.01
2005/0230314 A1* 10/2005 Kim .................... A61M 1/3403 210/646

(Continued)

FOREIGN PATENT DOCUMENTS

JP 2007-20801 A 2/2007
JP 2010-269050 A 12/2010

(Continued)

OTHER PUBLICATIONS

"Machine Translation of JP2007020801A", Toyoda et al., JP2007020801A, published 2007, 22 total pages. (Year: 2007).*

(Continued)

*Primary Examiner* — Jonathan M Peo
(74) *Attorney, Agent, or Firm* — Young Basile Hanlon & MacFarlane, P.C.

(57) ABSTRACT

Provided is a blood purification apparatus configured to keep a blood pump from being driven until a puncture needle is removed. The blood purification apparatus includes a blood circuit which is coupled with a puncture needle punctured into a patient and through which blood from the patient flows; a blood pump that is provided to the blood circuit and delivers liquid in the blood circuit by being driven; a needle removal detector that detects removal of the puncture needle from the patient; and a controller that starts a blood return process to return the blood in the blood circuit to the patient and puts the blood pump in a non-active state in response to determination that the blood return process ends.

11 Claims, 14 Drawing Sheets

(51) Int. Cl.

| | |
|---|---|
| ***A61M 60/113*** | (2021.01) |
| ***A61M 60/258*** | (2021.01) |
| ***A61M 60/37*** | (2021.01) |
| ***A61M 60/457*** | (2021.01) |

(52) U.S. Cl.
CPC ........ *A61M 60/113* (2021.01); *A61M 60/258* (2021.01); *A61M 60/37* (2021.01); *A61M 60/457* (2021.01)

(56) References Cited

U.S. PATENT DOCUMENTS

| | | | | |
|---|---|---|---|---|
| 2009/0095679 A1* | 4/2009 | Demers | A61M 1/362265 | 210/101 |
| 2014/0158589 A1* | 6/2014 | Furuhashi | A61M 1/1601 | 210/97 |
| 2017/0361003 A1* | 12/2017 | Toyoda | A61M 1/1601 | |

FOREIGN PATENT DOCUMENTS

| | | |
|---|---|---|
| JP | 2013-39241 A | 2/2013 |
| JP | 2016-165401 A | 9/2016 |

OTHER PUBLICATIONS

International Preliminary Report on Patentability for Application No. PCT/JP2021/027726, dated May 25, 2023, 6 pgs.

* cited by examiner

BLOOD PURIFICATION APPARATUS

CROSS-REFERENCE TO RELATED APPLICATION(S)

This application claims priority to International Application No. PCT/JP2021/027726-filed on Jul. 27, 2021 (published as WO2022/102175 on May 19, 2022), which claims priority to Japanese Application No. 2020-189213, filed on Nov. 13, 2020 (patent no. JP7536608), the entire disclosures of which are hereby incorporated by reference.

TECHNICAL FIELD

The present disclosure relates to a blood purification apparatus.

BACKGROUND ART

In a case where kidneys that constitute part of organs of a human do not operate normally (a renal failure), functions to produce urine out of extra water in the body, to excrete unwanted waste products in the body, and so forth do not work well. To deal with the renal failure, a blood purification apparatus (a dialysis apparatus) is used for conducting a therapy (a dialysis treatment) to extracorporeally circulate blood from a patient and to filter out waste products and water in the blood by using a blood purifier.

The blood purification apparatus withdraws blood from a patient and introduces the blood into the blood purifier (a blood flow route) through a blood circuit while introducing a dialysate from a dialysate supply source (a dialysate supplier) into the blood purifier (a dialysate flow route) through a dialysate circuit at the same time. The blood purification apparatus purifies the blood by exchanging components such as waste products and electrolytes between the blood and the dialysate through the blood purifier, and returns the purified blood to the body.

In the dialysis treatment, since the blood remains in the blood circuit after the blood is introduced into the blood circuit, a process to return the remaining blood to the body (a blood return process) is generally carried out by feeding normal saline or the dialysate into the blood circuit. The blood return process is carried out by delivering the liquid in the circuit by driving a blood pump provided to the blood circuit.

SUMMARY OF INVENTION

Usually, after the above-described blood return process ends, the blood pump may be driven in the following process; for example, as a post-process, a drainage process to extract the dialysate remaining in the blood circuit may be carried out. In the drainage process, it is necessary to remove a puncture needle punctured in a patient and then drive the blood pump. If the drainage process is started and the blood pump is driven while the puncture needle is left unremoved after the blood return process ends, there is a risk that air is mixed into the body or that the blood removal and the water removal may be carried out again.

An object of the present embodiment is to provide a blood purification apparatus that keep the blood pump from being driven until the puncture needle is removed after the blood return process ends.

A blood purification apparatus according to an embodiment includes a blood circuit which is coupled with a puncture needle punctured into a patient and through which blood from the patient flows; a blood pump that is provided to the blood circuit and delivers liquid in the blood circuit by being driven; a needle removal detector that detects removal of the puncture needle from the patient; and a controller that starts a blood return process to return the blood in the blood circuit to the patient and puts the blood pump in a non-active state in response to determination that the blood return process ends.

A method according to another embodiment is a method executed by a blood purification apparatus including a blood circuit which is coupled with a puncture needle punctured into a patient and through which blood from the patient flows, a blood pump that is provided to the blood circuit and delivers liquid in the blood circuit by being driven, and a needle removal detector that detects removal of the puncture needle from the patient, the method comprising the steps of: detecting removal of the puncture needle; starting a blood return process to return the blood in the blood circuit to the patient; and putting the blood pump in a non-active state in response to determination that the blood return process ends.

According to the blood purification apparatus of the embodiments, it is possible to prevent the blood pump from being driven while the puncture needle is left unremoved after the blood return process ends.

DESCRIPTION OF EMBODIMENTS

Blood purification apparatuses according to embodiments will be described below with reference to the accompanying drawings. A blood purification apparatus according to an embodiment prevents a blood pump provided to a blood circuit from being driven while a puncture needle is left unremoved after the end of a blood return process, which is carried out once dialysis treatment, hemodiafiltration treatment, and the like end. The blood return process is carried out by pushing the blood remaining in the blood circuit out to the body by introducing the dialysate and thereafter introducing air into the blood circuit.

First Embodiment

First, a first embodiment will be described. In the first embodiment, an example of carrying out the blood return process after dialysis treatment (HD), which is chronic blood purification therapy, is carried out for a chronic renal failure and the like will be mainly described. Note that, the dialysis treatment is merely an example of the chronic blood purification therapy, and the present embodiment may also be applied to hemofiltration treatment (HF), hemodiafiltration treatment (HDF), and the like.

Figure 1:
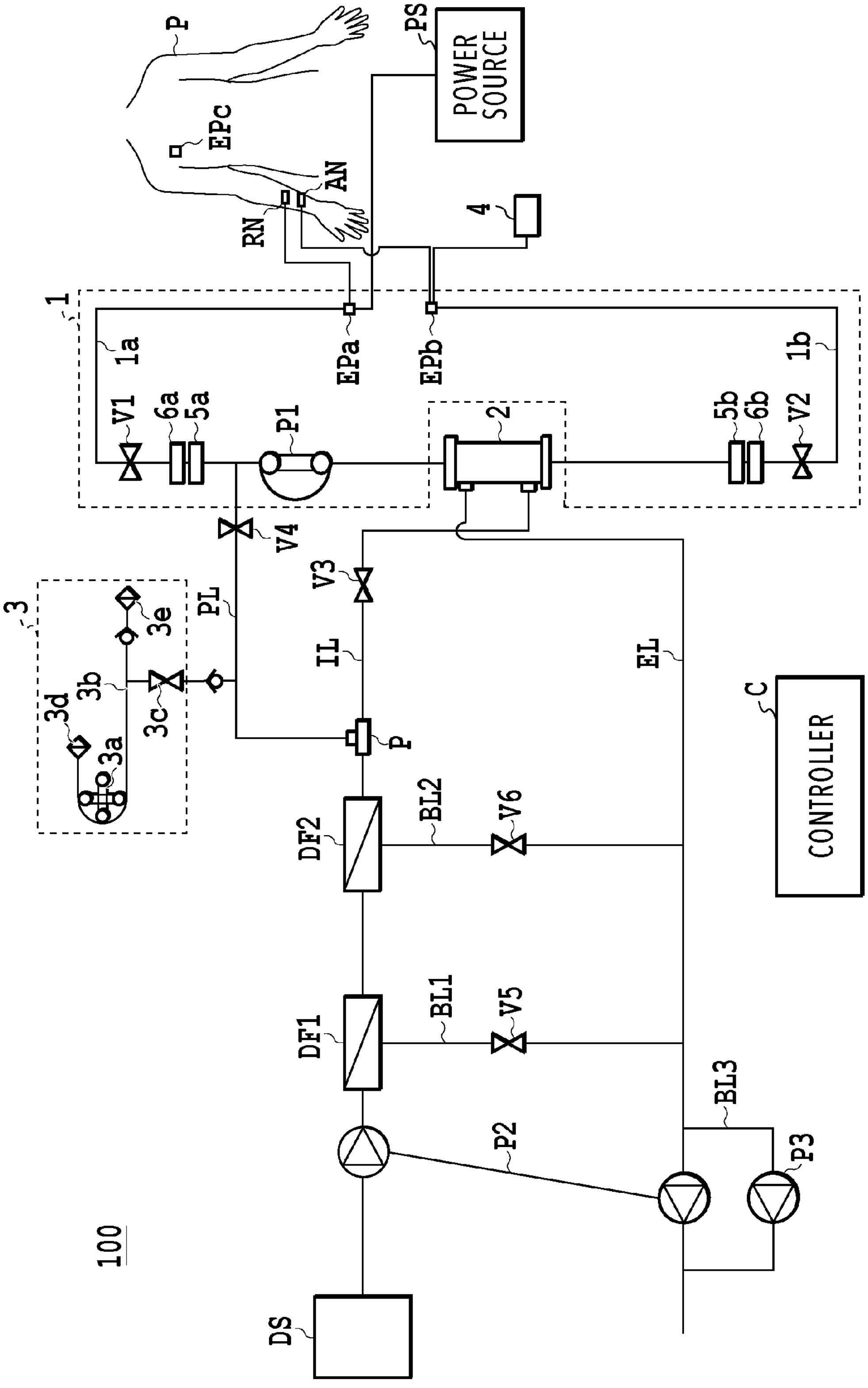
FIG. 1 is a piping diagram illustrating a configuration of a blood purification apparatus according to a first embodiment.

FIG. 1 is a piping diagram illustrating a configuration of a blood purification apparatus 100 according to the first embodiment. The blood purification apparatus 100 includes a blood circuit 1, a blood purifier 2, an air introducer 3, a needle removal detector 4, a blood concentration detector 5 (in the present embodiment, blood concentration detectors 5*a* and 5*b*), a bubble detector 6 (in the present embodiment, bubble detectors 6*a* and 6*b*), a dialysate introduction line IL, a drainage line EL, a priming liquid line PL, a water removal line RL, a bypass line BL (in the present embodiment, bypass lines BL1 and BL2), a blood pump P1, a dual pump P2, a water removal pump P3, a dialysate supplier DS, a dialysate filter DF (in the present embodiment, dialysate filters DF1 and DF2), a power source PS, an electrode EPa, an electrode EPb, an electrode EPc, and a controller C. Those constituents are merely examples, and other not-illustrated constituents may be included. Additionally, for example, some constituents such as the blood concentration detector 5 and the bubble detector 6 are not essential constituents.

The blood circuit 1 is a flow route that introduces the blood removed from a patient P into the blood purifier 2 and also returns the blood discharged from the purifier 2 (the purified blood) to the body at the time of the dialysis treatment. The blood circuit 1 is mainly formed from a tube that enables passage of the dialysate and the blood. The blood flows from a blood removal side puncture needle RN punctured in a blood removal side (an artery) of the patient P to a blood return side puncture needle AN punctured in a blood return side (a vein) of the patient P. The blood circuit 1 includes a blood removal side circuit 1*a* and a blood return side circuit 1*b*.

The blood removal side circuit 1*a* is a flow route that introduces the blood removed from the patient P into the blood purifier 2. One end of the blood removal side circuit 1*a* is attached to the blood removal side puncture needle RN, and the other end is joined to the blood purifier 2. An on-off valve (a solenoid valve) V1 is provided to the blood removal side circuit 1*a*. A flow of the blood in the blood removal side circuit 1*a* is controlled by opening and closing the on-off valve V1. The blood return side circuit 1*b* is a flow route that returns the blood discharged from the blood purifier 2 to the body. One end of the blood return side circuit 1*b* is attached to the blood return side puncture needle AN, and the other end is joined to the blood purifier 2. An on-off valve (a solenoid valve) V2 is provided to the blood return side circuit 1*b*. A flow of the blood in the blood return side circuit 1*b* is controlled by opening and closing the on-off valve V2.

The blood pump P1 is provided to the blood removal side circuit 1*a* and configured to deliver a liquid in the blood circuit 1 in a direction of movement from the blood removal side circuit 1*a* to the blood return side circuit 1*b* (hereinafter referred to as a normal direction in delivering liquid) or in a direction of movement from the blood return side circuit 1*b* to the blood removal side circuit 1*a* (hereinafter referred to as a reverse direction in delivering liquid). The blood pump P1 is formed from a peristaltic pump that includes a stator and a rotor, and the peristaltic pump is driven in such a way as to rotate the rotor. The rotor is rotated by an actuator (not illustrated) such as an electric motor under control of the controller C. The blood pump P1 is driven in accordance with a predetermined operation in the later-described blood return process and the like; however, the blood pump P1 is driven by also a manual operation by a user (for example, by pressing a not-illustrated manual button).

By forward rotation of the blood pump P1, the blood removal side circuit 1*a* pinched between the stator and the rotor is squeezed so as to generate the flow in the normal direction in delivering liquid. Additionally, by reverse rotation of the blood pump P1, the blood removal side circuit 1*a* is squeezed so as to generate the flow in the reverse direction in delivering liquid. In the blood pump P1, the number of rotation of the rotor is controlled and detected by closed-loop control using a pulse motor (not illustrated). Note that, instead of the closed-loop control using the pulse motor, the number of rotation of the rotor may be controlled by providing a rotary encoder to the blood pump P1 and detecting the rotation of the rotary encoder.

The blood purifier 2, which is also referred to as a dialyzer, purifies blood of the patient P. The blood purifier 2 includes a blood purification membrane (not illustrated) that is provided inside. The blood purification membrane is formed from a bundle of hollow fibers having pores on side walls (a hollow fiber membrane). An inner side of the blood purification membrane is a blood flow route (not illustrated), and an outer side of the blood purification membrane (the hollow fibers) is a dialysate flow route (not illustrated). The blood flowing in the blood purifier 2 flows in the blood flow route, and unwanted substances such as uremic substances are removed by passing through the pores in the blood purification membrane by one or both of diffusion and ultrafiltration. The dialysate flowing in the blood purifier 2 passes through the dialysate flow route, and the blood is supplemented only with substances such as electrolytes included in the dialysate, which are necessary for a human body, while the substances pass through the pores. Note that, the inner side of the blood purification membrane can also function as the dialysate flow route, and the outer side of the blood purification membrane can also function as the blood flow route.

The dialysate introduction line IL is a flow route from a dialysate supplier to the blood purifier 2 that supplies the blood purifier 2 with the dialysate from the dialysate supplier DS. The dialysate introduction line IL is mainly formed from a tube that enables passage of the dialysate. An on-off valve (a solenoid valve) V3 and a dialysate port P are provided to the dialysate introduction line IL. A flow of the dialysate into the blood purifier 2 is controlled by opening and closing the on-off valve V3. The dialysate port P takes out the dialysate. The blood circuit 1 and the dialysate introduction line IL are coupled to each other through the blood purification membrane of the blood purifier 2 and are configured to bidirectionally circulate the blood and the dialysate.

The drainage line EL is a flow route from the blood purifier 2 to a drainer (not illustrated) that drains the dialysate drained from the blood purifier 2. The drainage line EL is mainly formed from a tube that enables passage of the drainage. The water removal line RL is a flow route from the drainage line EL to the drainer that removes water from the blood in the blood purifier 2. The water removal line RL is mainly formed from a tube that enables passage of the drainage.

The dual pump P2 is provided across the dialysate introduction line IL and the drainage line EL. The dual pump P2 introduces the dialysate to a downstream side in the liquid delivery direction of the dialysate introduction line IL, and meanwhile, drains the drainage of the dialysate to a downstream side in the liquid delivery direction of the drainage line EL. In other words, the dual pump P2 plays roles as a dialysate supply pump for supplying the dialysate to the blood circuit 1 and as a drainage pump for draining the dialysate from the drainer. A plunger (not illustrated) is provided inside a housing of the dual pump P2. A volume on the dialysate introduction line IL side and a volume on the drainage line EL side are defined while interposing the plunger in between, and the introduction of the dialysate and the discharge of the drainage are interlocked with reciprocation of the plunger.

Note that, a configuration in which the dialysate supply pump (not illustrated) is provided to the dialysate introduction line IL and the drainage pump (not illustrated) is provided to the drainage line EL instead of the dual pump P2 may be applied. In this case, the dialysate supply pump and the drainage pump are each formed from a peristaltic pump that includes a stator and a rotor, and the peristaltic pump is driven in such a way as to rotate the rotor. The rotor is rotated by an actuator (not illustrated) such as an electric motor under control of the controller C. By driving (rotation) of the dialysate supply pump, the dialysate introduction line IL pinched between the stator and the rotor is squeezed so as to generate the flow of the dialysate. The same applies to the drainage pump.

The water removal pump P3 is provided to the water removal line RL. The water removal pump P3 drains water in the blood from the water removal line RL in order to remove the water from the blood in the blood purifier 2. Since the amounts of the dialysate introduced into and the dialysate drained from the blood purifier 2 become equal to each other by driving the dual pump P2, the water from the blood in the blood purifier 2 is removed by driving the water removal pump P3.

The priming liquid line PL is a connection flow route that connects the dialysate introduction line IL and the blood circuit 1 with each other and introduces priming liquid (the dialysate) into the blood circuit 1 and the blood purifier 2. Specifically, the priming liquid line PL is a flow route from the dialysate port P to the blood removal side circuit 1*a*. An on-off valve (a solenoid valve) V4 is provided to the priming liquid line PL. A flow of the priming liquid to the blood removal side circuit 1*a* is controlled by opening and closing the on-off valve V4.

A priming process to remove the air in the circuit is carried out by filling the blood circuit 1 and the blood purifier 2 with the priming liquid (by replacing the air in the circuit with the priming liquid) before the dialysis treatment. In the priming process, the priming liquid flows in the priming liquid line PL and is introduced into the blood circuit 1 and the blood purifier 2 by opening the on-off valve V4 and closing the on-off valve V3.

In the present embodiment, both the dialysate introduction line IL and priming liquid line PL are used for introducing the dialysate into the blood circuit 1 in the blood return process. In other words, the dialysate introduction line IL and the priming liquid line PL play a role as a dialysate introduction circuit for introducing the dialysate into the blood circuit 1. Additionally, the priming liquid line PL is used for introducing the air into the blood circuit 1 in the blood return process. In other words, the priming liquid line PL plays a role as an air introduction circuit that introduces the air into the blood circuit 1. Moreover, the drainage line EL is used for delivering the drainage from the blood circuit 1 in the drainage process after the blood return process is carried out. Details thereof will be described later.

Each of the bypass line BL1 and the bypass line BL2 is a flow route from the dialysate introduction line IL to the drainage line EL. An on-off valve (a solenoid valve) V5 is provided to the bypass line BL1. Likewise, an on-off valve (a solenoid valve) V6 is provided to the bypass line BL2. A flow of the dialysate from the dialysate introduction line IL to the drainage line EL is controlled by opening and closing the on-off valves V5 and V6.

The bypass line BL1 and the bypass line BL2 are the flow routes for preventing the inappropriate dialysate from flowing into the blood circuit 1. For example, the blood purification apparatus 100 is provided with a warmer (not illustrated) for warming the dialysate. In the case where the temperature of the dialysate exceeds a predetermined temperature due to the warmer at the time of the dialysis treatment, the dialysate flows to the drainage line EL through the bypass line BL1 and the bypass line BL2 in order to prevent the dialysate at the high temperature from flowing to the blood circuit 1. In this case, the on-off valves V5 and/or V6 are opened.

The air introducer 3 introduces the air into the blood circuit 1 (the blood removal side circuit 1*a*) through the priming liquid line PL. The air introducer 3 is coupled to the priming liquid line PL. The air introducer 3 plays roles in pushing the dialysate introduced into the blood circuit 1 through the dialysate introduction line IL and the priming liquid line PL out to the blood return side circuit 1*b* (or the blood removal side circuit 1*a*) and returning the blood in the blood circuit 1 to the patient P. Details thereof will be described later.

The air introducer 3 includes an air pump 3*a*, an air introduction route 3*b*, an on-off valve (a solenoid valve) 3*c*, an air filter 3*d*, and an air filter 3*e*. The air pump 3*a* incorporates a rotor and drives the rotor so as to perform rotation. The rotor is rotated by an actuator (not illustrated) such as an electric motor under control of the controller C. In the air pump 3*a*, the number of rotation of the rotor is controlled and detected by closed-loop control using a pulse motor (not illustrated). Note that, instead of the closed-loop control using the pulse motor, the number of rotation of the rotor may be controlled by providing a rotary encoder to the air pump 3*a* and detecting the rotation of the rotary encoder.

The air is introduced into the blood circuit 1 through the priming liquid line PL through the air introduction route 3*b* by driving the air pump 3*a*. The on-off valve 3*c* is provided between the air introduction route 3*b* and the priming liquid line PL. A flow of the air to the priming liquid line PL is controlled by opening and closing the on-off valve 3*c*. The air filter 3*d* and the air filter 3*e* trap and remove bacteria and dust in the air.

Note that, in the present embodiment, the air introducer 3 is coupled to the priming liquid line PL; however, it is not limited to such a configuration. The air introducer 3 may be coupled to a rehydration line (not illustrated). The rehydration line is, for example, a flow route that introduces the dialysate to the blood circuit to rehydrate to the blood in order to increase the filtration amount of the blood from the patient in the hemodiafiltration treatment. In a case where this configuration is employed, the air from the air introducer 3 is introduced into the blood circuit 1 through the rehydration line.

The dialysate filter DF (the dialysate filters DF1 and DF2) purifies the dialysate by trapping substances such as endotoxins contained in the dialysate supplied from the dialysate supplier DS. Each dialysate filter DF is provided to the dialysate introduction line IL and includes a primary chamber and a secondary chamber (not illustrated). Additionally, a dialysate purification membrane is provided inside the dialysate filter DF1. The dialysate purification membrane is formed from a bundle of hollow fibers (a hollow fiber membrane) with side walls provided with pores. The dialysate filter DF is configured such that the dialysate flows from the primary chamber (an inner side of the dialysate purification membrane) to the secondary chamber (an outer side of the dialysate purification membrane). The dialysate filter DF has a property of blocking passage of the air with surface tension of water molecules by passing water thereto.

The (blood removal side) electrode EPa is provided to the blood removal side circuit 1*a*. The (blood return side) electrode EPb is provided to the blood return side circuit 1*b*. The electrode EPa and the electrode EPb are formed from a conductor coupled to a flexible tube, and the electrode EPa is electrically coupled to the power source PS by coupling means such as a crocodile clip. Additionally, the electrode EPb is electrically coupled to the needle removal detector 4. Note that, the electrode EPa and the electrode EPb are not put in contact with the blood physically but are electrically coupled with the blood through the blood circuit 1.

The power source PS applies a voltage to be a weak current (equal to or less than 1 mA) at high frequencies (few kHz to tens of kHz) to the electrode EPa. The current flows in the blood of the patient P through the blood removal side puncture needle RN and the blood return side puncture needle AN with the power source PS applying the voltage to the electrode EPa. Since the blood that extracorporeally circulates through the blood removal side circuit 1*a* and the blood return side circuit 1*b* is a conductor that allows the current to flow therein, as long as the blood removal side puncture needle RN and the blood return side puncture needle AN are normally punctured in the patient P, the current flows in the blood of the patient P through the blood removal side puncture needle RN and the blood return side puncture needle AN.

The (body surface side) electrode EPc is attached to the body surface (skin) of the patient P to be closely attached. The electrode EPc is formed from an electrode attached to be closely attached to a position in which the heart is interposed between the electrode and the puncture portions of the blood removal side puncture needle RN and the blood return side puncture needle AN, and the electrode EPc detects an electric signal from the body of the patient P. Additionally, the electrode EPc is electrically coupled to the needle removal detector 4 (in FIG. 1, the coupling state is not illustrated). The electrode EPc is, for example, used for measuring an electrocardiogram (biological information) from the patient P in the dialysis treatment.

Figure 2:
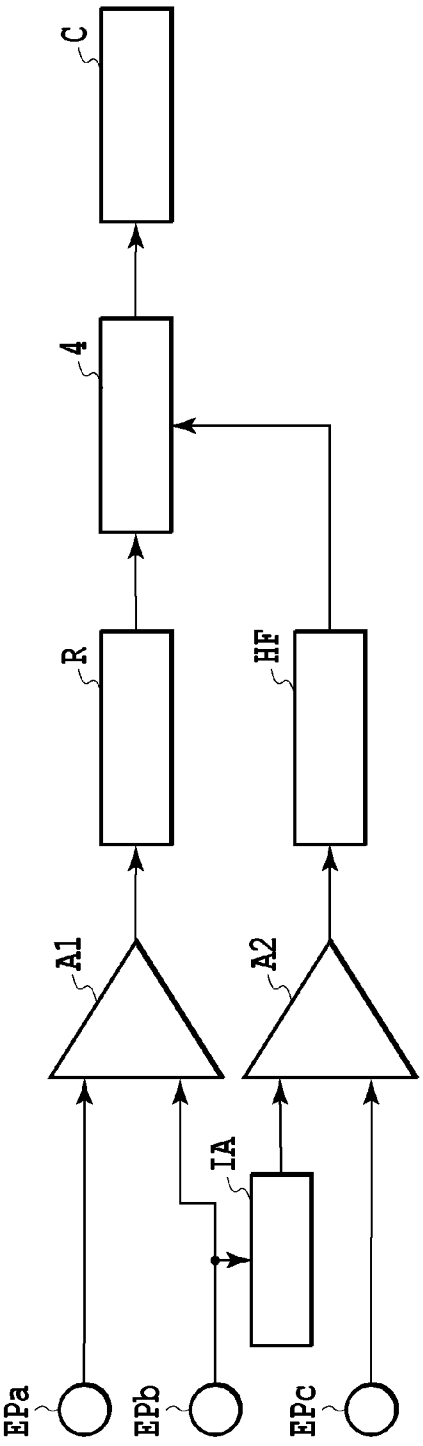
FIG. 2 is a diagram illustrating a relationship between a needle removal detector, an electrode, and a controller.

The needle removal detector 4 detects removal of the blood removal side puncture needle RN and/or the blood return side puncture needle AN punctured in the patient P. The needle removal detector 4 is coupled with the controller C. FIG. 2 illustrates a relationship between the needle removal detector 4, the electrode EPa, the electrode EPb, the electrode EPc, and the controller C.

As illustrated in FIG. 2, the electrode EPa and the electrode EPb are coupled to a differential amplification circuit A1 while the electrode EPb is coupled to an impedance adjustment circuit IA. Additionally, the electrode EPc and the impedance adjustment circuit IA are coupled to a differential amplification circuit A2. The impedance adjustment circuit IA adjusts the impedance in the measured voltage inputted to the differential amplification circuit A1 and the impedance in the measured voltage inputted to the differential amplification circuit A2. Since the“impedance of the blood” obtained from the electrode EPa and the electrode EPb and the “impedance of body fluid and impedance of skin” obtained from the electrode EPb and the electrode EPc have a difference, the impedance adjustment circuit IA adjusts this difference. As the impedance adjustment circuit IA, preferably, a circuit that adjusts a load resistance by a variable resistance and the like or a circuit that makes adjustment by using automatic gain control (AGC) such that heartbeat components can be extracted is applied.

The differential amplification circuit A1 generates an electric signal in which the voltage difference between the measured voltage from the electrode EPa and the measured voltage from the electrode EPb is amplified. The differential amplifier A2 generates an electric signal in which the voltage difference between the measured voltage from the electrode EPc and the measured voltage from the impedance adjustment circuit IA is amplified.

Additionally, the differential amplification circuit A1 is coupled to the needle removal detector 4 through a rectifier circuit R. The differential amplification circuit A2 is coupled to the needle removal detector 4 through a high cut filter HF. The high cut filter HF removes the high-frequency contents applied by the power source PS from the electric signal generated by the differential amplification circuit A2. The electric signal generated by the differential amplification circuit A1 is inputted to the needle removal detector 4, and the electric signal generated by the differential amplification circuit A2 is inputted to the needle removal detector 4.

The needle removal detector 4 obtains a predetermined biological parameter (in the present embodiment, the electrocardiogram) by detecting a change in the impedance in the body of the patient P based on the electric signal inputted from the differential amplification circuit A2. That is, in the present embodiment, a pair of the electrode EPb and the electrode EPc detects the electric signal from the body of the patient P, and the needle removal detector 4 obtains in real-time the electrocardiogram as the biological parameter based on the detected electric signal. Additionally, the needle removal detector 4 monitors in real-time the current flowing in the electrode EPb and also monitors the change in the impedance in the body of the patient P detected by the needle removal detector 4.

The controller C is a processing apparatus that controls the constituents of the blood purification apparatus 100 including control of driving of the blood pump P1 described above. The controller C includes an arithmetic apparatus and a storage apparatus (a storage apparatus such as a RAM and a ROM). The arithmetic apparatus may be implemented by a processor such as a CPU and a microcontroller, an ASIC (application specific integrated circuit), an FPGA (field programmable gate array), and the like; however, its mode is not limited.

The signal indicating the current value and the change in the impedance monitored and detected by the needle removal detector 4 is transmitted to the controller C. The controller C determines whether the blood removal side puncture needle RN and/or the blood return side puncture needle AN are removed from the patient P based on the signal indicating the current value and the change in the impedance. In a case where the blood removal side puncture needle RN and/or the blood return side puncture needle AN are removed from the patient P, the current from the power source PS does not reach the electrode EPb, and the needle removal detector 4 detects no current (a waveform corresponding to the current value is interrupted). Additionally, likewise, no change in the impedance is detected. According to such a state, the controller C determines that the blood removal side puncture needle RN and/or blood return side puncture needle AN are removed from the patient P.

Note that, in the present embodiment, the power source PS applies the voltage to the electrode EPa, and the needle removal detector 4 monitors the current flowing in the electrode EPb; however, the voltage may be applied to either one or both of the electrode EPa and the electrode EPb. In a case where the voltage is applied to the electrode EPb, the power source PS is coupled to the electrode EPb. Additionally, the needle removal detector 4 may monitor the current flowing in either one or both of the electrode EPa and the electrode EPb. In a case where the current flowing in the electrode EPa is monitored, the electrode EPa is coupled to the needle removal detector 4.

The blood concentration detector 5 (the blood concentration detector 5*a* and the blood concentration detector 5*b*) detects the concentration of the blood flowing in the blood circuit 1. The blood concentration detector 5*a* is provided to the blood removal side circuit 1*a*, and the blood concentration detector 5*b* is provided to the blood return side circuit 1*b*. The blood concentration detector 5*a* and the blood concentration detector 5*b* are, for example, implemented by an infrared ray radiator that radiates an infrared ray and an infrared ray sensor that detects the light. The amount of the infrared ray that passes through the blood is changed in accordance with the amount of red blood cells. Accordingly, it is possible to detect the concentration of the blood flowing in the blood circuit 1 by detecting the light amount of the infrared ray that passes through the blood. The detected light amount of the infrared ray is transmitted to the controller C. The controller C determines whether the light amount exceeds a predetermined threshold.

The concentration of the blood flowing in the blood circuit 1 detected by the blood concentration detector 5 is a reference for determining the returned blood flow rate in the blood return process. Details will be described later. Note that, in the present embodiment, the blood concentration detector 5*a* and the blood concentration detector 5*b* are provided respectively; however, only either one of the blood concentration detector 5*a* and the blood concentration detector 5*b* may be provided. In a case where the blood return process in the normal direction in delivering liquid is carried out, preferably, the blood concentration detector 5*b* is provided to the blood return side circuit 1*b*. On the other hand, in a case where the blood return process in the reverse direction in delivering liquid described later, preferably, the blood concentration detector 5*a* is provided to the blood removal side circuit 1*a*.

The bubble detector 6 (the bubble detector 6*a* and the bubble detector 6*b*) detects that bubbles are generated in the blood and/or the dialysate flowing in the blood circuit 1 in the blood return process. The bubble detector 6*a* is provided to the blood removal side circuit 1*a*, and the bubble detector 6*b* is provided to the blood return side circuit 1*b*. The bubble detector 6*a* and the bubble detector 6*b* are, for example, implemented by an ultrasonic radiator that radiates ultrasonic and an ultrasonic sensor that detects the ultrasonic.

The ultrasonic sensor detects a voltage in accordance with the vibration of the blood and/or the dialysate. The bubbles have a higher attenuation rate than that of the blood and/or the dialysate. Accordingly, the bubble detector 6 can detect the generation of the bubbles by determining that the voltage value falls below a predetermined threshold. The detected voltage value is transmitted to the controller C. The controller C determines whether the voltage value exceeds a predetermined threshold.

The bubbles generated in the blood circuit 1 detected by the bubble detector 6 are a reference for ending the blood return process in the middle. Details will be described later. Note that, in the present embodiment, the bubble detector 6*a* and the bubble detector 6*b* are provided respectively; however, only either one of the bubble detector 6*a* and the bubble detector 6*b* may be provided. In a case where the blood return process in the normal direction in delivering liquid is carried out, preferably, the bubble detector 6*b* is provided to the blood return side circuit 1*b*. On the other hand, in a case where the blood return process in the reverse direction in delivering liquid described later, preferably, the bubble detector 6*a* is provided to the blood removal side circuit 1*a*.

Figure 3:
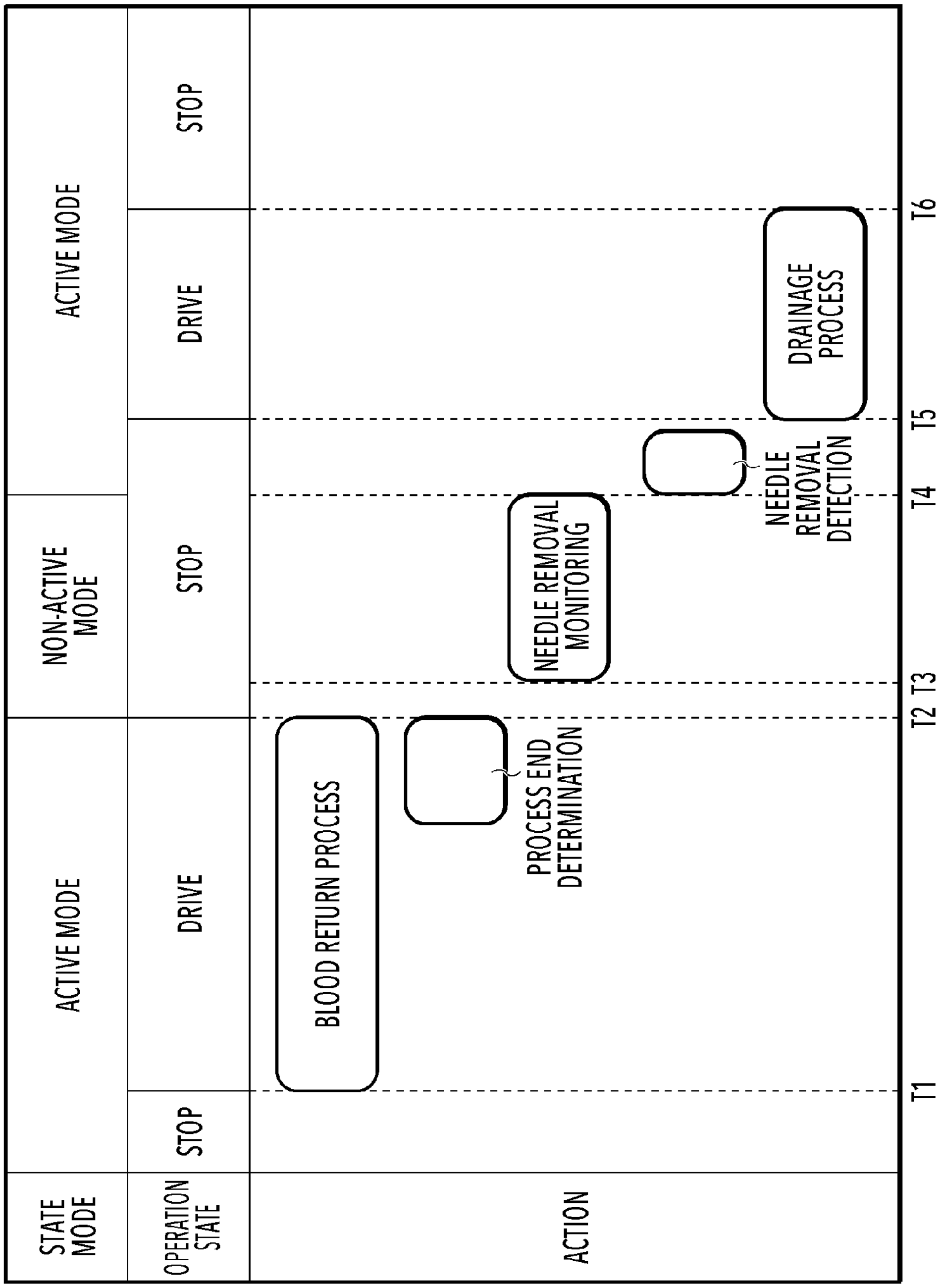
FIG. 3 is a diagram illustrating a relationship between a state mode and an operation state of a blood pump.

Next, with reference to FIG. 3, a relationship between a state mode and a driving state of the blood pump P1 is described. In the present embodiment, the blood pump P1 is in a non-active state until the needle removal is detected after the blood return process ends and is in an active state once the needle removal is detected. The non-active state means that the blood pump P1 is not driven even with a manual operation by the user and the like. In other words, the blood pump P1 is not driven unless being in the active state. The above-described two states are managed as two state modes, an "active mode" and a "non-active mode", with the controller C implementing a state machine. The state modes are stored in a register (not illustrated).

The controller C instructs the blood pump P1 to be driven only in a case where the state mode is the active mode with reference to the state modes stored in the register. Accordingly, if the state mode is the active mode, the blood pump P1 is driven according to a predetermined operation under control of the controller C at the time of the dialysis treatment and the blood return process. Additionally, if the state mode is the active mode, the blood pump P1 is driven by the instruction by the controller C in response to the manual operation by the user (for example, by pressing a not-illustrated manual (driving) button).

On the other hand, if the state mode is the non-active mode, the controller C does not instruct the blood pump P1 to be driven by pressing the driving button. In other words, if the state mode is the non-active mode, the blood pump P1 is locked so as not to be driven.

FIG. 3 illustrates transition of the state mode and an operation state for a predetermined action regarding the blood pump P1. The operation state indicates whether the blood pump P1 is driven or stopped. In the example illustrated in FIG. 3, the state mode transitions between the active mode and the non-active mode in accordance with the actions carried out in time points T1 to T6, and the blood pump P1 is in either of a driving state and a stop state. Note that, although it is not illustrated in FIG. 3, the dialysis treatment is carried out before the time point T1.

As illustrated in FIG. 3, the state mode for the blood pump P1 is the active mode as the initial (default) state mode. Under such a state mode, once the blood return process is started in the time point T1, the blood pump P1 is driven (rotated) (transitions from the stop state to the driving state) by the instruction of the controller C. In the blood return process according to the present embodiment, first, the dialysate is introduced into the blood circuit 1 (the dialysate introduction stage), and thereafter the air is introduced into the blood circuit 1 (the air introduction stage).

Figure 4:
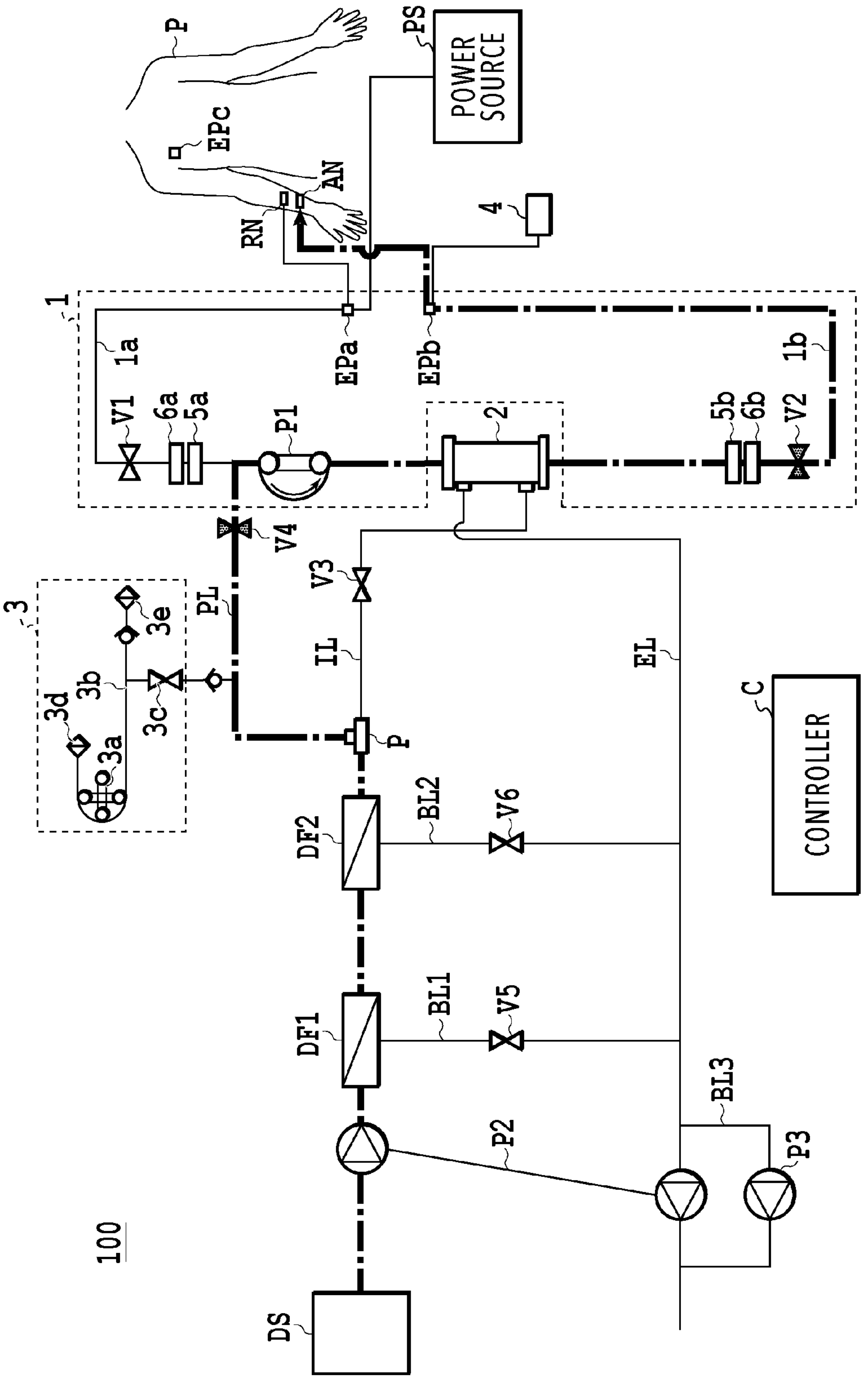
FIG. 4 is a diagram illustrating a flow of dialysate in a dialysate introduction stage according to the first embodiment.
Figure 5:
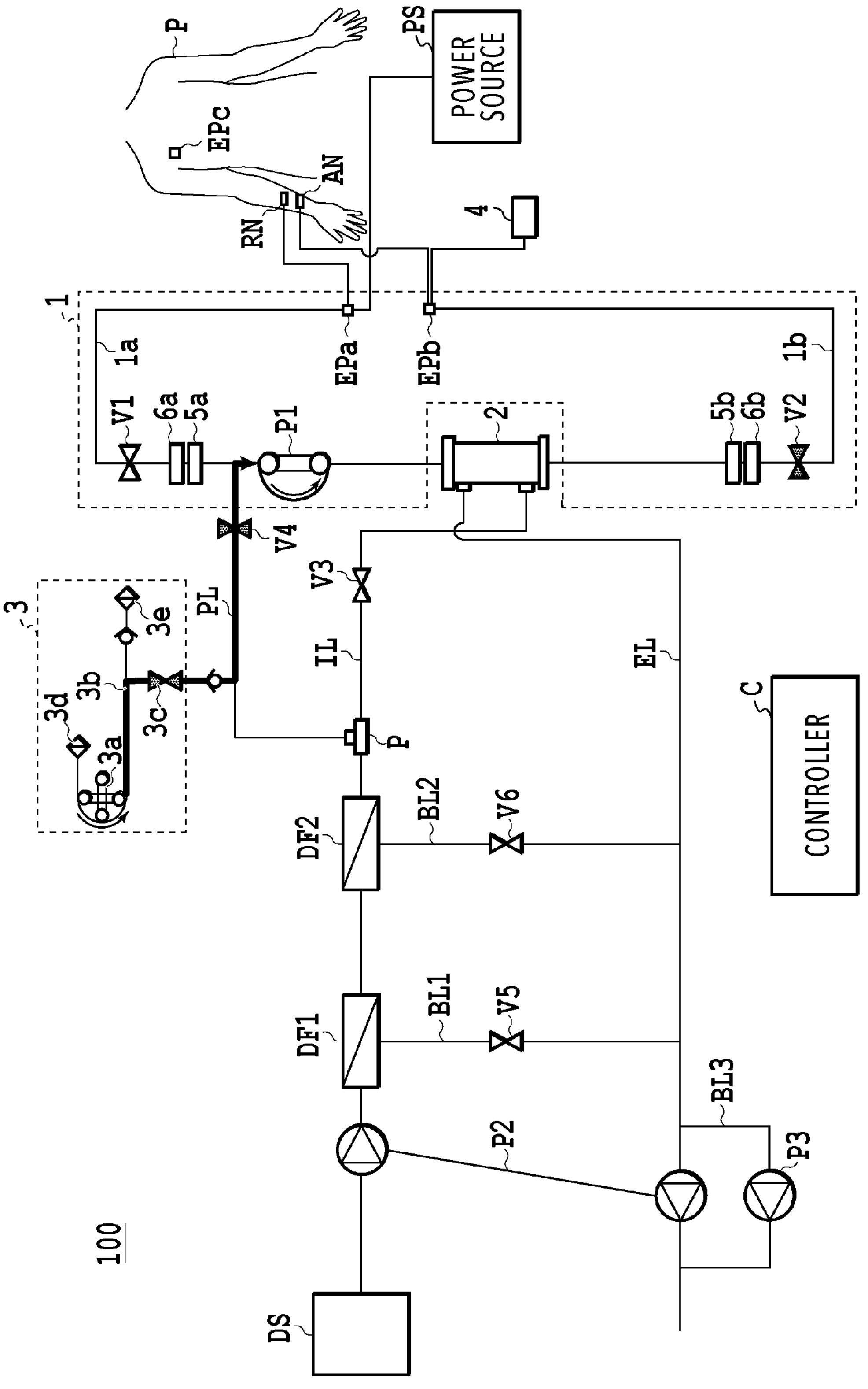
FIG. 5 is a diagram illustrating a flow of the dialysate and air in an air introduction stage according to the first embodiment.

FIG. 4 illustrates a flow of the dialysate in the dialysate introduction stage in the blood return process. FIG. 5 illustrates a flow of the dialysate and the air in the air introduction stage. In FIGS. 4 and 5, in a case where the on-off valves are opened, the on-off valves illustrated in the drawings are indicated with hatching, and in a case where the on-off valves are closed, the on-off valves illustrated in the drawings are indicated with outlines. The drawings of FIG. 6 and following described later are shown similarly.

In the dialysate introduction stage illustrated in FIG. 4, the on-off valve V4 and the on-off valve V2 are opened under control of the controller C. Additionally, the blood pump P1 rotates forward. Moreover, the dual pump P2 is driven. With this, the dialysate from the dialysate supplier passes through the dialysate introduction line IL, the priming liquid line PL, the blood removal side circuit 1*a*, the blood purifier 2, and the blood return side circuit 1*b*. In FIG. 4, this flow of the dialysate is indicated with an arrow of a thick chain line. By this flow of the dialysate, the dialysate pushes out the blood remaining in the blood purifier 2 and the blood circuit 1 (the blood return side circuit 1*b*), and the blood is returned to the body. In such a state, once a predetermined amount of the dialysate flows in the blood circuit 1, the process is switched to the air introduction stage.

Once the process is switched to the air introduction stage illustrated in FIG. 5, driving of the dual pump P2 is stopped under control of the controller C. Instead, the air pump 3*a* is driven. With this, the air passes through the air introduction route 3*b*, the priming liquid line PL, the blood removal side circuit 1*a*, the blood purifier 2, and the blood return side circuit 1*b*. In FIG. 5, this flow of the air is indicated with an arrow of a thick solid line. By this flow of the air, the blood remaining in the blood purifier 2 and the blood circuit 1 is pushed out through the dialysate introduced into the blood circuit 1 in the dialysate introduction stage, and the blood is returned to the body.

In the blood return process described above, since the blood return is carried out by introducing the air into the blood circuit 1, it is possible to reduce the amount of the dialysate used for the blood return comparing with a case of carrying out the blood return by using only the dialysate. Additionally, since the air is introduced into the blood circuit 1 after the dialysate is introduced into the blood circuit 1, the air pushes out the blood to the body through the dialysate, and thus it is possible to prevent the air from being taken into the patient P.

Referring back to FIG. 3. Once the blood return process illustrated in FIG. 4 or 5 ends, in other words, once the controller C determines that the blood return process ends in the time point T2, the state mode regarding the blood pump P1 transitions to the non-active mode by the instruction of the controller C, and driving of the blood pump P1 is stopped (transitions from the driving state to the stop state). The end of the blood return process is determined based on, for example, whether a certain period of time elapses and/or whether the returned blood flow rate reaches a predetermined threshold.

Whether a certain period of time elapses may be determined by the controller C based on the time measured by a timer from the start of the blood return process. Whether the returned blood flow rate reaches a predetermined threshold may be determined by the controller C based on whether the number of rotation of the blood pump P1 exceeds the threshold (the number of rotation of the blood pump P1 is detected by the above-described closed-loop control). Additionally, whether the returned blood flow rate reaches a predetermined threshold may be determined by the controller C based on whether the concentration of the blood flowing in the blood circuit 1 falls below a threshold (the concentration of the blood flowing in the blood circuit 1 is detected by the blood concentration detector 5).

Additionally, once determining that the blood return process ends, the controller C instructs the power source PS and the needle removal detector 4 to detect (monitor) the removal of the blood removal side puncture needle RN and/or the blood return side puncture needle AN. In the time point T3, once the needle removal monitoring is started, the power source PS applies the voltage to the electrode EPa, the current flows between the electrode EPa and the electrode EPb, and the needle removal detector 4 detects the current through the patient P. Since the needle removal detector 4 cannot detect the electric conduction between the electrodes (or does not detect the change in the impedance from the electrode EPc) once the needle removal is carried out, the needle removal detector 4 transmits an indicator that indicates the detection of the non-electric conduction to the controller C, and the controller C determines that the needle removal is carried out based on the indicator.

In a case where the state mode regarding the blood pump P1 is the non-active mode, for example, the blood pump P1 is not driven even if the driving button is pressed by the user. In such a state, the state mode does not transition to the active mode and the blood pump P1 is not driven until the removal of the puncture needle is detected.

Thereafter, once the removal of the puncture needle is detected, in other words, once the controller C determines that the needle removal is carried out in the time point T4, the state mode regarding the blood pump P1 transitions to the active mode by the instruction of the controller C. In a case where the state mode is in the active mode, for example, once the driving button is pressed by the user, the blood pump P1 is driven.

Once the blood return process ends, and the removal of the puncture needle is detected, the drainage process for extracting the dialysate remaining in the blood circuit 1 is carried out. In the example illustrated in FIG. 3, the drainage process is carried out in a time point of the time point T5. The drainage process may be automatically started under control of the controller C in response to the end of the blood return process and the detection of the needle removal or may be started by a manual operation by the user.

Figure 6:
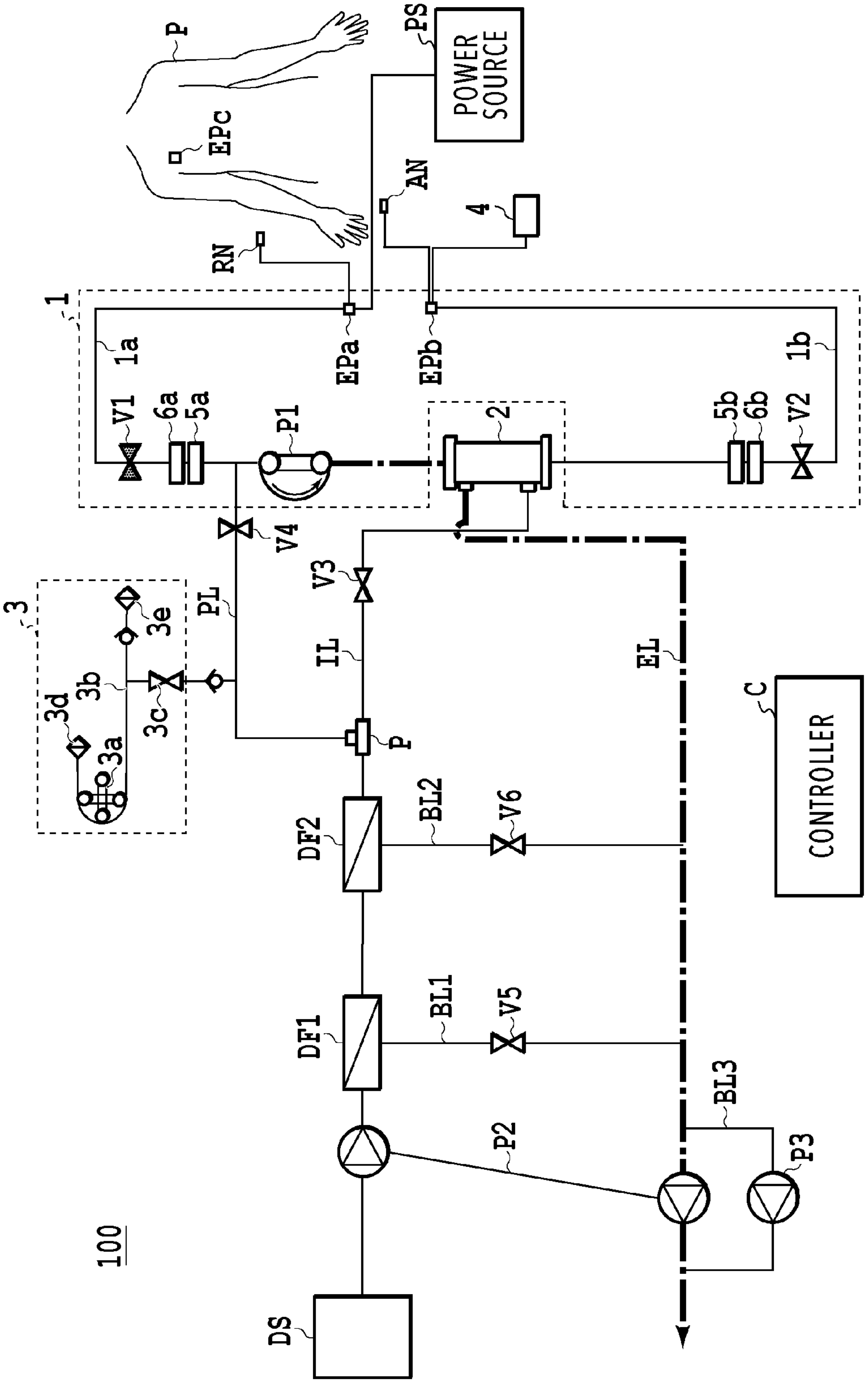
FIG. 6 is a diagram illustrating a flow of drainage in a drainage process.

FIG. 6 illustrates a flow of the drainage (the dialysate) in the drainage process. The drainage process illustrated in FIG. 6 introduces the air from the puncture needle RN and drains the liquid remaining in the blood removal side circuit 1*a* to the drainage line EL by rotating the blood pump P1 forward. In this drainage process, the on-off valve V1 is opened under control of the controller C. Additionally, the blood pump P1 rotates forward. With this, the dialysate (the drainage) remaining in the blood removal side circuit 1*a* and the blood purifier 2 passes through the blood removal side circuit 1*a*, the blood purifier 2, and the drainage line EL. In FIG. 6, this flow of the dialysate is indicated with an arrow of a thick chain line. In this way, the drainage is drained to a transparent drainer.

Note that, instead of carrying out the above-described drainage process, a process (a manual process) to detach the blood circuit 1 joined to the blood pump P1 may be carried out. In this detaching process, it is also necessary to rotate the rotor of the blood pump P1 manually to detach the blood circuit 1. In other words, the blood pump P1 is driven also in the detaching process of the blood circuit 1. Additionally, the drainage process illustrated in FIG. 6 is merely an example, and the blood return process to drain the liquid remaining in the blood return side circuit 1*b* to the drainage line EL may be carried out, for example.

According to the present embodiment, in response to the end of the blood return process, the detection of the removal of the puncture needle is monitored, and the blood pump P1 is controlled so as not to be driven (set to non-active) until the needle removal is detected. This makes it possible to prevent the drainage process or the detaching process of the blood circuit 1 from being started while the needle is left unremoved after the end of the blood return process, thereby preventing the blood pump P1 from being driven.

Figure 7:
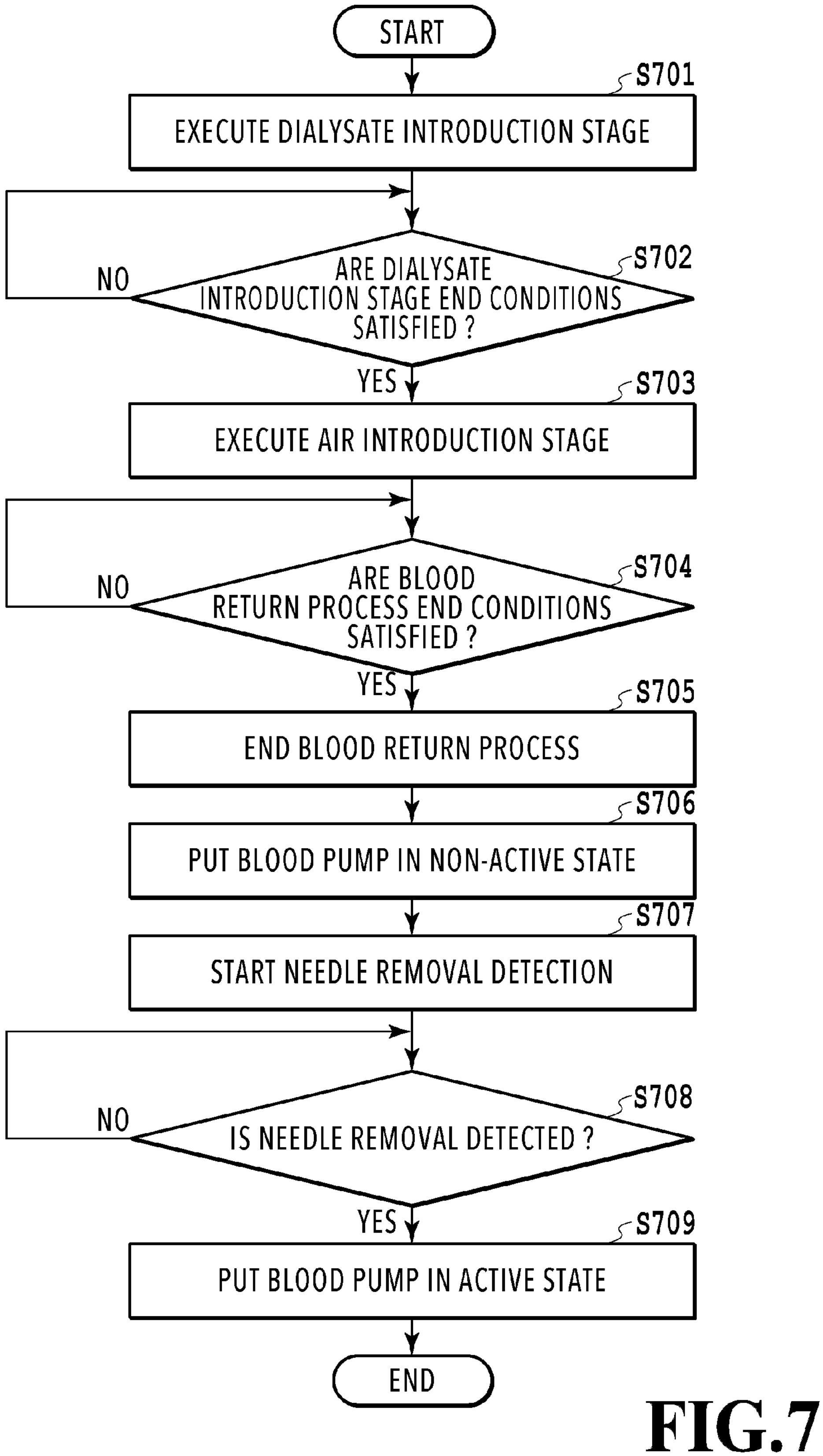
FIG. 7 is a flowchart illustrating processing according to the first embodiment.

Next, processing according to the first embodiment is described with reference to a flowchart illustrated in FIG. 7. The processing illustrated in FIG. 7 corresponds to the processing from carrying out of the blood return process to the detection of the needle removal described in FIG. 3. Although it is not illustrated, the dialysis treatment is carried out before the blood return process. Additionally, the operation mode regarding the blood pump P1 described in FIG. 3 is the active mode (the state mode indicating the active mode is stored in the register).

First, the controller C instructs the on-off valves (the on-off valve V4 and the on-off valve V2), the blood pump P1, and the dual pump P2 to execute the dialysate introduction stage in the blood return process. In response to this instruction, the on-off valves are opened, the blood pump P1 rotates forward, and the dual pump P2 is driven (step S701). In this way, the dialysate from the dialysate supplier is introduced into the blood circuit 1 as described in FIG. 4.

Next, the controller C determines whether the dialysate introduction stage end conditions are satisfied (step S702). The processing in step S702 is repeated until the dialysate introduction stage end conditions are satisfied.

The dialysate introduction stage end conditions may include elapse of a certain period of time after the dialysate introduction stage is started and/or reaching of the returned blood flow rate to a predetermined threshold. As described above, whether a certain period of time elapses may be determined by the controller C based on the time measured by the timer from the start of the dialysate introduction stage. Whether the returned blood flow rate reaches a predetermined threshold may be determined by the controller C based on whether the number of rotation of the blood pump P1 exceeds a predetermined threshold. Additionally, whether the returned blood flow rate reaches a predetermined threshold may be determined by the controller C based on whether the concentration of the blood flowing in the blood circuit 1 falls below a predetermined threshold (the concentration of the blood flowing in the blood circuit 1 is detected by the blood concentration detector 5).

Once determining that the dialysate introduction stage end conditions are satisfied, the controller C instructs the on-off valve (the on-off valve 3*c*), the dual pump P2, and the air pump 3*a* to execute the air introduction stage in the blood return process. In response to the instruction, driving of the dual pump P2 is stopped. Additionally, the on-off valve 3*c* is opened, and the air pump 3*a* is rotated (step S703). In this way, the air from the air introducer 3 is introduced into the blood circuit 1 as described in FIG. 5.

Next, the controller C determines whether the air introduction stage end conditions (the blood return process end conditions) are satisfied (step S704). The processing in step S704 is repeated until the blood return process end conditions are satisfied.

The blood return process end conditions include elapse of a certain period of time after the dialysate introduction stage (or the air introduction stage) is started and/or reaching of the returned blood flow rate to a predetermined threshold. Additionally, the blood return process end conditions may include detection of no blood flowing in the blood circuit 1 and/or detection of the bubbles in the blood circuit 1. Detection of no blood flowing in the blood circuit 1 may be determined by the controller C based on whether the concentration of the blood flowing in the blood circuit 1 falls below a predetermined threshold (the concentration of the blood flowing in the blood circuit 1 is detected by the blood concentration detector 5). Additionally, detection of the bubbles in the blood circuit 1 may be determined by the controller C based on whether the voltage in accordance with the vibration of the blood and/or dialysate flowing in the blood circuit 1 due to ultrasonic falls below a predetermined threshold (the voltage is detected by the bubble detector 6).

Once determining that the blood return process end conditions are satisfied, the controller C instructs the on-off valves (the on-off valve 3*c*, the on-off valve V4, and the on-off valve V2), the blood pump P1, and the air pump 3*a* to end the blood return process. In response to this instruction, the on-off valves are closed, and driving of the blood pump P1 and the air pump 3*a* is stopped (step S705).

Next, the controller C puts the blood pump P1 in the non-active state (step S706). Specifically, the operation mode regarding the blood pump P1 transitions to the non-active mode (the operation mode stored in the register is updated to the non-active mode). The blood pump P1 is locked so as not to be driven by the processing in step S706.

Next, the controller C instructs the power source PS and the needle removal detector 4 to start the detection (monitoring) of the removal of the puncture needle (the blood removal side puncture needle RN and the blood return side puncture needle AN). In response to this instruction, the power source PS applies the voltage to the electrode EPa. Additionally, the needle removal detector 4 detects the current flowing in the blood of the patient P and/or the change in the impedance in the body of the patient P (step S707).

Next, the controller C determines whether the needle removal is detected (step S708). The processing in step S708 is repeated until the needle removal is detected. The reference of determining whether the needle removal is carried out is as described above.

Once carrying out of the needle removal is detected, the blood pump P1 is put in the active state (step S709). Specifically, the operation mode regarding the blood pump P1 transitions to the active mode (the operation mode stored in the register is updated to the active mode). The blood pump P1 can be driven by the instruction of the controller C by the processing in step S709. Thereafter, the drainage process or the detaching process of the blood pump P1 described above is executed.

As above, the blood purification apparatus 100 according to the first embodiment is described. According to the first embodiment, after the blood return process ends, the blood pump P1 is in the non-active state until the needle removal is detected; thus, it is possible to prevent the drainage process and the like from being started while the puncture needle is left unremoved.

In the present embodiment, the needle removal monitoring (in other words, step S707 illustrated in FIG. 7) is executed after the blood return process ends; however, the timing of the start of the needle removal monitoring may not be after the blood return process ends. The needle removal monitoring may be started before the blood return process is started (for example, at the time of the dialysis treatment) or may be executed in the timing of the start of the blood return process. In other words, the needle removal monitoring may be started in any timing and is at least executed in the timing of the end of the blood return process.

Note that, in the present embodiment, the blood return process is carried out by introducing the air into the blood circuit 1 after the dialysate is introduced into the blood circuit 1; however, the blood return may be carried out only by introducing the dialysate into the blood circuit 1 without introducing the air into the blood circuit 1. In this case, the blood return process is carried out by the flow of the dialysate illustrated in FIG. 4, and the blood return process ends by determining that the blood return process end conditions described in FIG. 7 (step S704) are satisfied.

Additionally, the configuration described in the present embodiment in which the needle removal is monitored and detected is merely an example, and the configuration using the electrode EPc is not an essential configuration. At least, a configuration for detecting the removal of the blood removal side puncture needle RN and/or the blood return side puncture needle AN based on the electric conduction state between the two electrodes provided in the blood removal side circuit 1*a* and the blood return side circuit 1*b* is employed.

Second Embodiment

Figure 8:
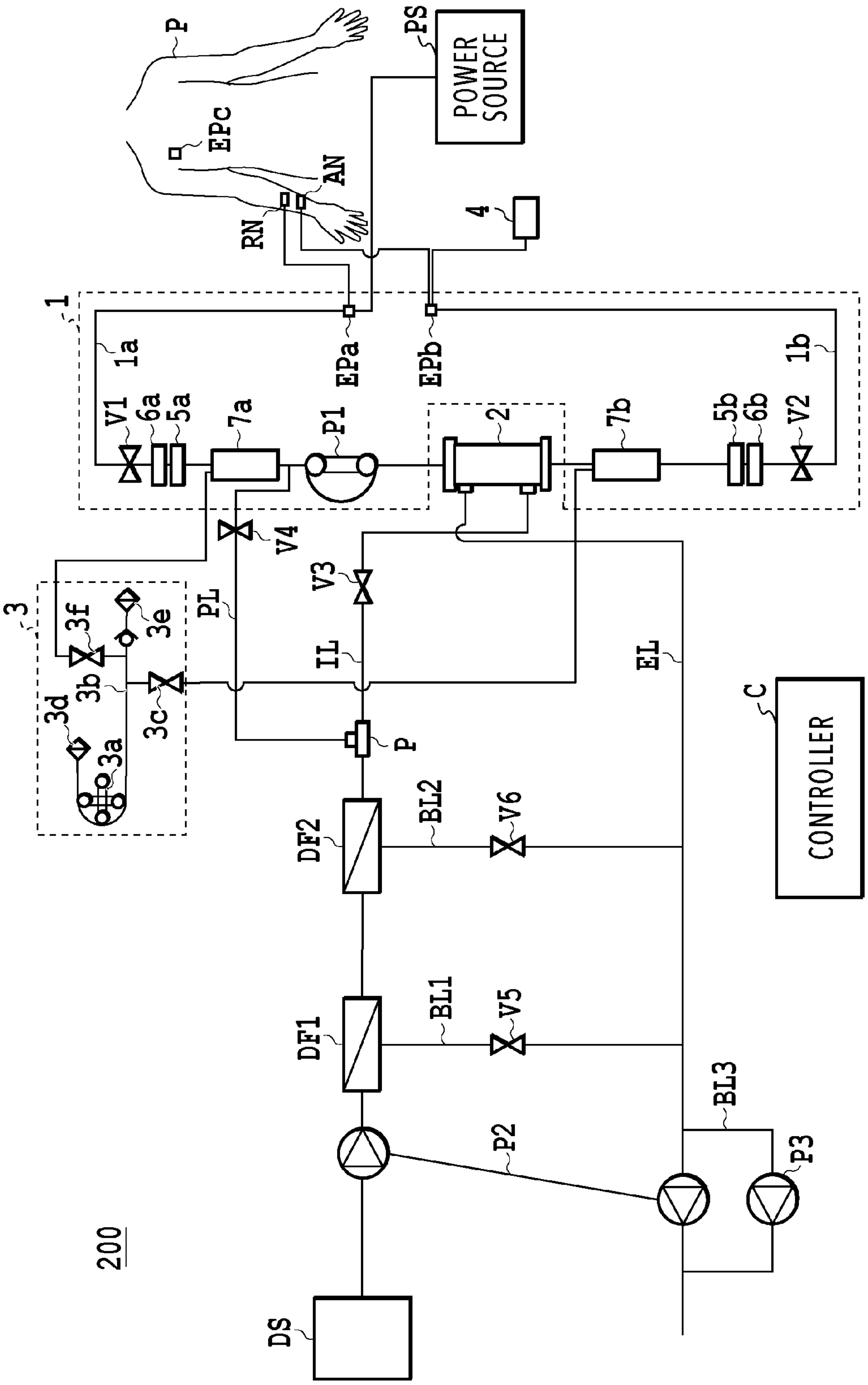
FIG. 8 is a piping diagram illustrating a configuration of a blood purification apparatus according to a second embodiment.

Next, a second embodiment is described. In the second embodiment, an example of carrying out the blood return process after the dialysis treatment is carried out as the chronic blood purification therapy is described. The second embodiment is different from the first embodiment in only the blood return process. In the blood return process according to the second embodiment, the air introducer 3 directly introduces the air into the blood circuit 1. FIG. 8 is a piping diagram illustrating a configuration of a blood purification apparatus 200 according to the second embodiment. The blood purification apparatus 200 has the same configuration as the blood purification apparatus 100 according to the first embodiment except the different configuration of the air introducer 3 and that a blood removal side air trap chamber 7*a* and a blood return side air trap chamber 7*b* are further included.

As illustrated in FIG. 8, the blood removal side air trap chamber 7*a* is provided to the blood removal side circuit 1*a*, and the blood return side air trap chamber 7*b* is provided to the blood return side circuit 1*b*. The blood removal side air trap chamber 7*a* is provided for a main object that the air is trapped so as to prevent the air that can be generated by driving the blood pump P1 from not flowing into the blood purifier 2 in the dialysis treatment and the like. The blood return side air trap chamber 7*b* is provided for a main object that the air is trapped so as to prevent the above-described air from flowing into the body of the patient through the blood circuit 1. In other words, both the blood removal side air trap chamber 7*a* and blood return side air trap chamber 7*b* play roles as chambers that store the blood in the blood circuit 1.

The air introducer 3 (the air introduction route 3*b*) is coupled to the blood removal side air trap chamber 7*a* and the blood return side air trap chamber 7*b* and introduces the air into the blood removal side air trap chamber 7*a* and the blood return side air trap chamber 7*b*. Each of the blood removal side air trap chamber 7*a* and the blood return side air trap chamber 7*b* includes two layers, a blood layer and an air layer, and once the chamber is filled with the air, the liquid level is lowered, and there is a risk that air lock occurs that causes the air to enter the hollow fibers of the blood purifier 2.

In the example illustrated in FIG. 8, the air introducer 3 (the air pump 3*a*) lowers the liquid level by introducing the air into the blood return side air trap chamber 7*b* by forward rotation and raises the liquid level by draining the air from the blood return side air trap chamber 7*b* by reverse rotation. Likewise, the air introducer 3 (the air pump 3*a*) lowers the liquid level by introducing the air into the blood removal side air trap chamber 7*a* by forward rotation, and raises the liquid level by draining the air from the blood removal side air trap chamber 7*a* by reverse rotation.

The air introducer 3 further includes an on-off valve (a solenoid valve) 3*f*. The on-off valve 3*f* is provided between the air introduction route 3*b* and the blood removal side air trap chamber 7*a*. A flow of the air from the air introducer 3 to the blood removal side air trap chamber 7*a* is controlled by opening and closing the on-off valve 3*f* (the air introducer 3 feeds the air into the blood removal side air trap chamber 7*a*). A flow of the air from the air introducer 3 to the blood return side air trap chamber 7*b* is controlled by opening and closing the on-off valve 3*c* (the air introducer 3 feeds the air into the blood return side air trap chamber 7*b*).

As described above, the air introducer 3 plays a role as a liquid level adjustment pump for the blood removal side air trap chamber 7*a* and the blood return side air trap chamber 7*b* in the dialysis treatment and the like (in other words, other than the blood return process) (usually, the liquid level adjustment pump is not used for the blood return). On the other hand, the air introducer 3 plays roles in introducing the air into the blood circuit 1 to return the blood in the blood circuit 1 and the blood purifier 2 to the body in the blood return process.

Figure 9:
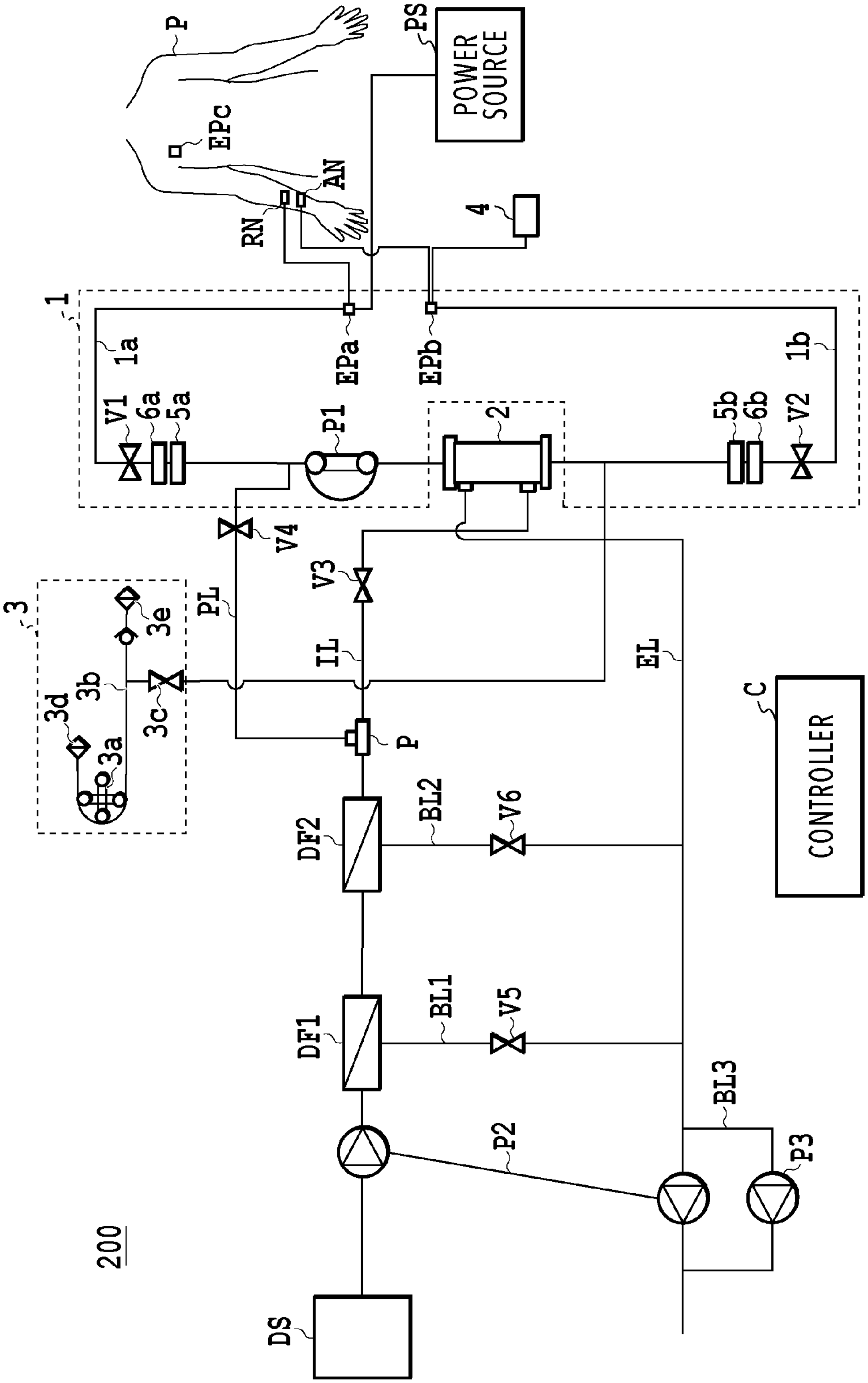
FIG. 9 is a piping diagram illustrating a configuration of the blood purification apparatus according to the second embodiment.
Figure 10:
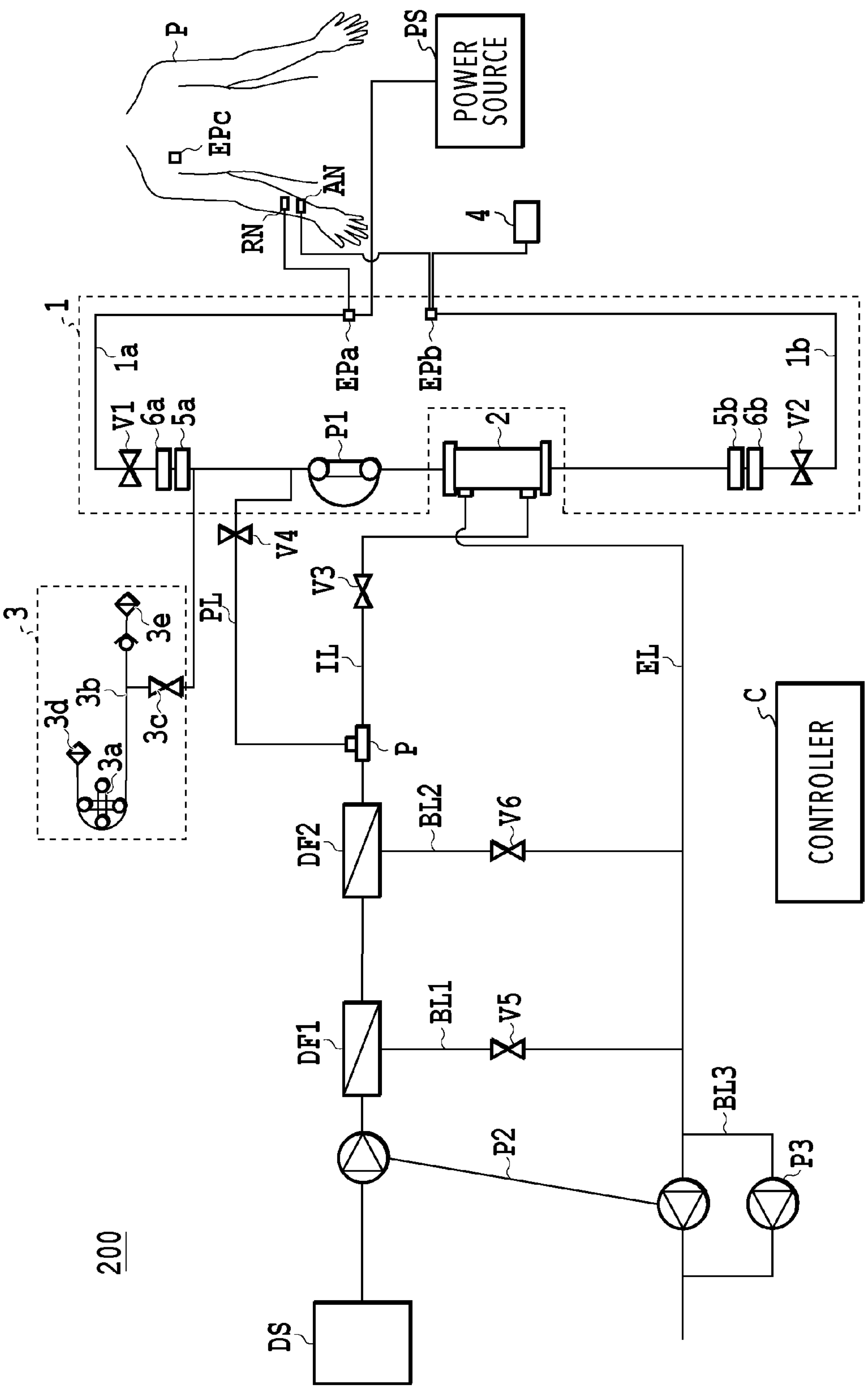
FIG. 10 is a piping diagram illustrating a configuration of the blood purification apparatus according to the second embodiment.

Note that, the blood removal side air trap chamber 7*a* and the blood return side air trap chamber 7*b* are not essential configurations. For example, in a case where the blood removal side air trap chamber 7*a* and the blood return side air trap chamber 7*b* are not provided, the air introducer 3 may be coupled to the blood return side circuit 1*b* as illustrated in FIG. 9, or the air introducer 3 may be coupled to the blood removal side circuit 1*a* as illustrated in FIG. 10. Additionally, both the blood removal side air trap chamber 7*a* and the blood return side air trap chamber 7*b* do not necessarily need to be provided, and only one of them may be provided.

Figure 11:
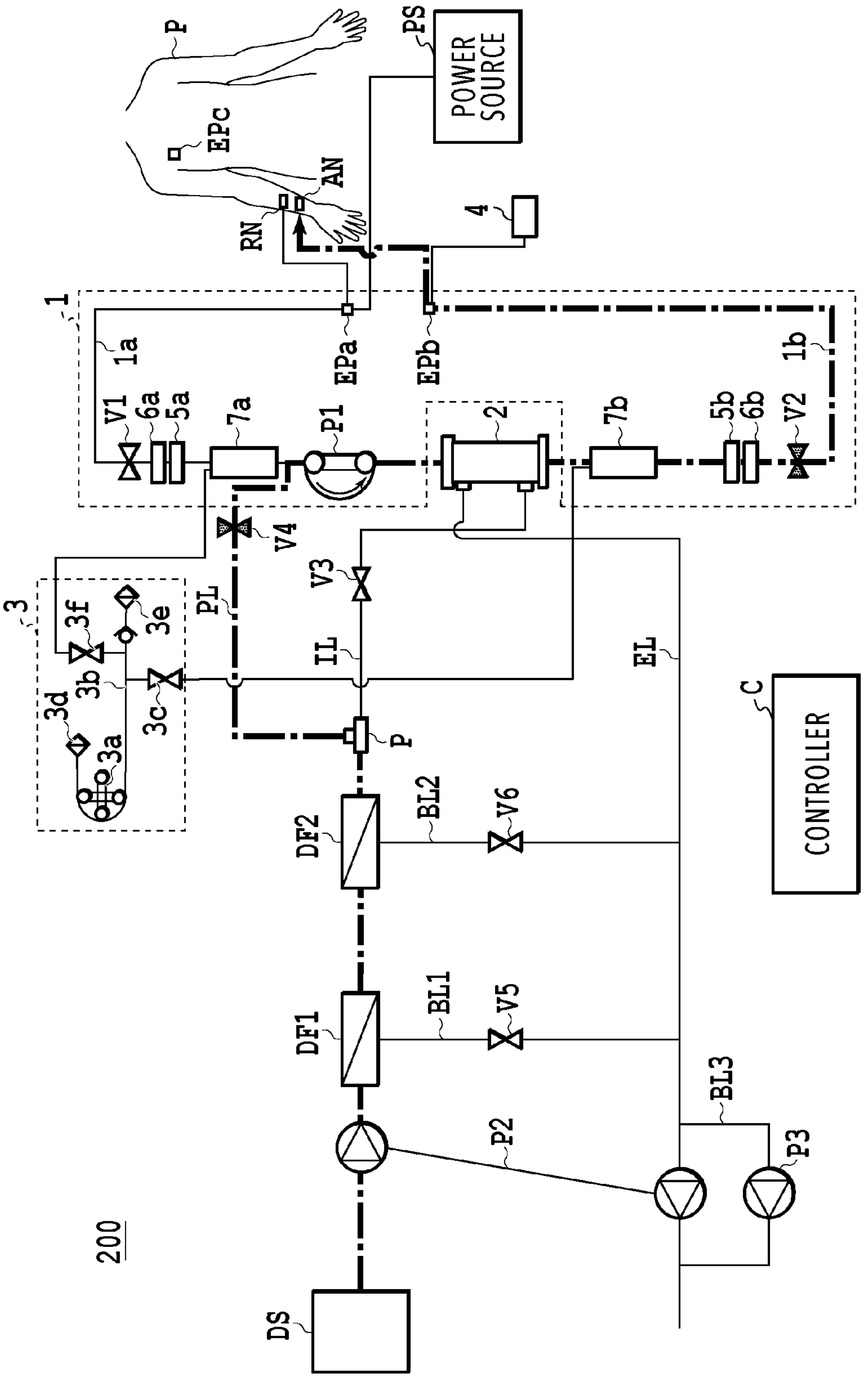
FIG. 11 is a diagram illustrating a flow of dialysate in a dialysate introduction stage according to the second embodiment.
Figure 12:
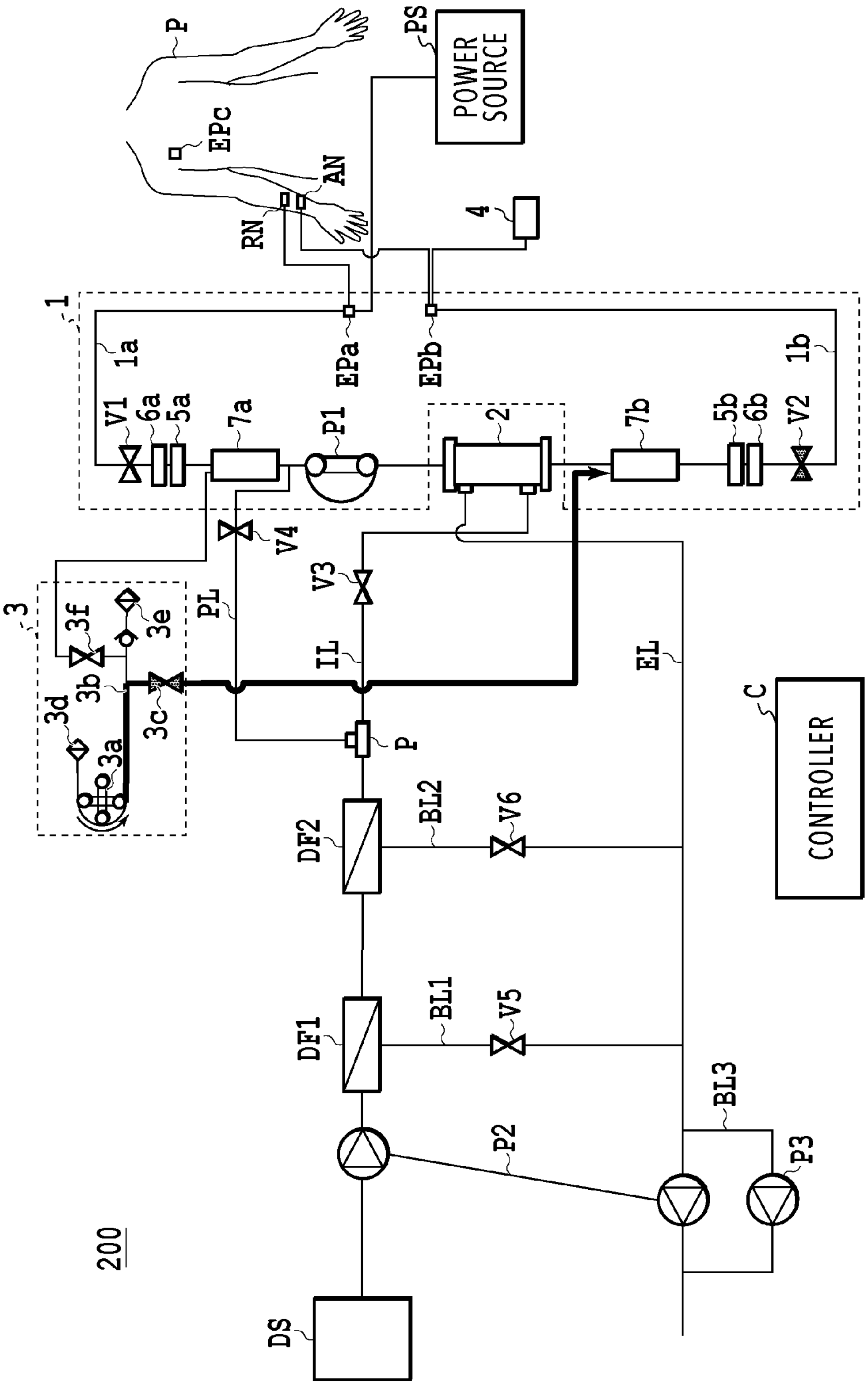
FIG. 12 is a diagram illustrating a flow of the dialysate and air in an air introduction stage according to the second embodiment.
Figure 13:
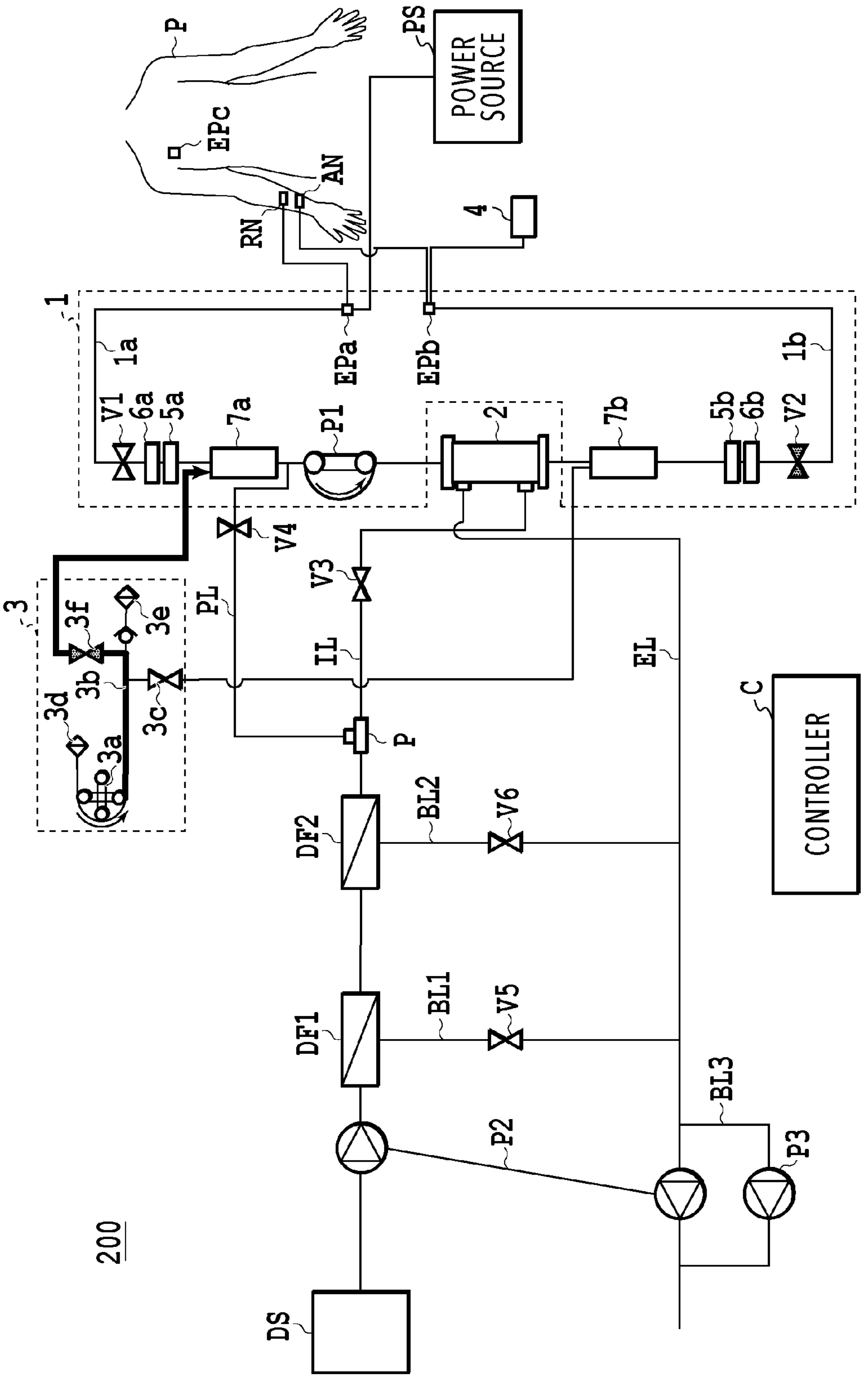
FIG. 13 is a diagram illustrating a flow of the dialysate and the air in the air introduction stage according to the second embodiment.

Next, the blood return process according to the second embodiment is described with reference to FIGS. 11 to 13. In the blood return process according to the second embodiment, in the configuration described in FIG. 8, first, the dialysate is introduced into the blood circuit 1 (the dialysate introduction stage), and thereafter the air is introduced into the blood circuit 1 (the air introduction stage). FIG. 11 illustrates the dialysate introduction stage. FIG. 12 illustrates the air introduction stage in which the air introducer 3 introduces the air into the blood return side circuit 1*b*. In FIG. 13, the air introduction stage in which the air introducer 3 introduces the air into the blood removal side circuit 1*a* is illustrated. Either one of the two air introduction stages illustrated in FIGS. 12 and 13 is carried out after the dialysate introduction stage illustrated in FIG. 11.

FIG. 11 illustrates a flow of the dialysate in the dialysate introduction stage. FIG. 12 illustrates a flow of the dialysate and the air in the air introduction stage in which the air is introduced into the blood return side circuit 1*b*. FIG. 13 illustrates a flow of the dialysate and the air in the air introduction stage in which the air is introduced into the blood removal side circuit 1*a*. In the following diagrams, in a case where the on-off valves are opened, the on-off valves illustrated in the drawings are indicated with hatching, and in a case where the on-off valves are closed, the on-off valves illustrated in the drawings are indicated with outlines.

In the dialysate introduction stage illustrated in FIG. 11, the on-off valve V4 and the on-off valve V2 are opened under control of the controller C. Additionally, the blood pump P1 rotates forward. Moreover, the dual pump P2 is driven. With this, the dialysate from the dialysate supplier passes through the dialysate introduction line IL, the priming liquid line PL, the blood removal side circuit 1*a*, the blood purifier 2, and the blood return side circuit 1*b*. In FIG. 11, this flow of the dialysate is indicated with an arrow of a thick chain line. By this flow of the dialysate, the dialysate pushes out the blood remaining in the blood purifier 2 and the blood circuit 1 (the blood return side circuit 1*b*), and the blood is returned to the body. In such a state, once a predetermined amount of the dialysate flows in the blood circuit 1, the process is switched to the air introduction stage.

Once the process is switched to the air introduction stage illustrated in FIG. 12 in which the air is introduced into the blood return side circuit 1*b*, the on-off valve V4 is closed, and driving of the blood pump P1 and the dual pump P2 is stopped under control of the controller C. Instead, the on-off valve 3*c* is opened. Additionally, the air pump 3*a* is driven. With this, the air passes through the air introduction route 3*b* and the blood return side circuit 1*b*. In FIG. 12, this flow of the air is indicated with an arrow of a thick solid line. By this flow of the air, the blood remaining in the blood circuit 1 is pushed out through the dialysate introduced into the blood circuit 1 in the dialysate introduction stage, and the blood is returned to the body.

Once the process is switched to the air introduction stage illustrated in FIG. 13 in which the air is introduced into the blood removal side circuit 1*a*, the on-off valve V4 and the on-off valve 3*c* are closed, and driving of the dual pump P2 is stopped under control of the controller C. Instead, the on-off valve 3*f* is opened. Additionally, the air pump 3*a* is driven. With this, the air passes through the air introduction route 3*b*, the blood removal side circuit 1*a*, the blood purifier 2, and the blood return side circuit 1*b*. In FIG. 13, this flow of the air is indicated with an arrow of a thick solid line. By this flow of the air, the blood remaining in the blood purifier 2 and the blood circuit 1 is pushed out through the dialysate introduced into the blood circuit 1 in the dialysate introduction stage, and the blood is returned to the body.

In the configuration illustrated in FIG. 13, the air introducer 3 is coupled to the blood removal side air trap chamber 7*a*, and the air introducer 3 introduces the air into the blood circuit 1; however, the blood pump P1 may play a role of the air introducer 3. The air pump P1 introduces the air into the blood return side circuit 1*b* if the forward rotation is continued also after all the dialysate introduced from the priming liquid line PL passes through the air pump P1 in the dialysate introduction stage. Accordingly, in this case, the air introducer 3 may not be provided.

As described above, the air introducer 3 plays a role as the liquid level adjustment pump at the time of the dialysis treatment and also plays roles in introducing the air into the blood circuit 1 for the blood return in the blood return process. The blood pump P1 plays roles in delivering the dialysate in the blood circuit 1 and also plays roles in introducing the air into the blood circuit 1 for the blood return in the air introduction stage in the blood return process.

Note that, the dialysate introduction stage end conditions and the blood return process end conditions in the second embodiment are similar to the conditions described in the first embodiment. Additionally, the processing to carry out transition of the state modes regarding the blood pump P1 is also similar to the processing described in the first embodiment.

As above, the blood purification apparatus 200 according to the second embodiment is described. In the second embodiment, it is also possible to prevent the drainage process and the like from being started while the puncture needle is left unremoved, and it is possible to reduce the amount of the dialysate used for the blood return comparing with a case of carrying out the blood return by using only the dialysate.

Third Embodiment

Next, a third embodiment is described. In the third embodiment, an example of carrying out the blood return process after apheresis therapy, which removes a disease-causing substance of acute disorder, is carried out as acute blood purification therapy will be mainly described. Note that, the apheresis therapy is merely an example of the acute blood purification therapy, and the present embodiment may be applied to continuous renal replacement therapy (CRRT), intermittent renal replacement therapy (IRRT), and the like.

The apheresis therapy is a treatment method of carrying out plasma exchange and the like for separating and removing a pathogenic substance in the blood. In the apheresis therapy, a double-lumen catheter may be used as vascular access for temporary blood purification. The third embodiment is different from the first embodiment in a structure of the needle removal detector in accordance with a use of a puncture needle having the double-lumen structure. Accordingly, only the configurations of the needle removal detector and the puncture needle are described in the third embodiment. The configurations of the needle removal detector and the puncture needle indicated in the present embodiment may be applied to an acute blood purification apparatus used for the acute blood purification therapy such as the apheresis treatment.

Figure 14:
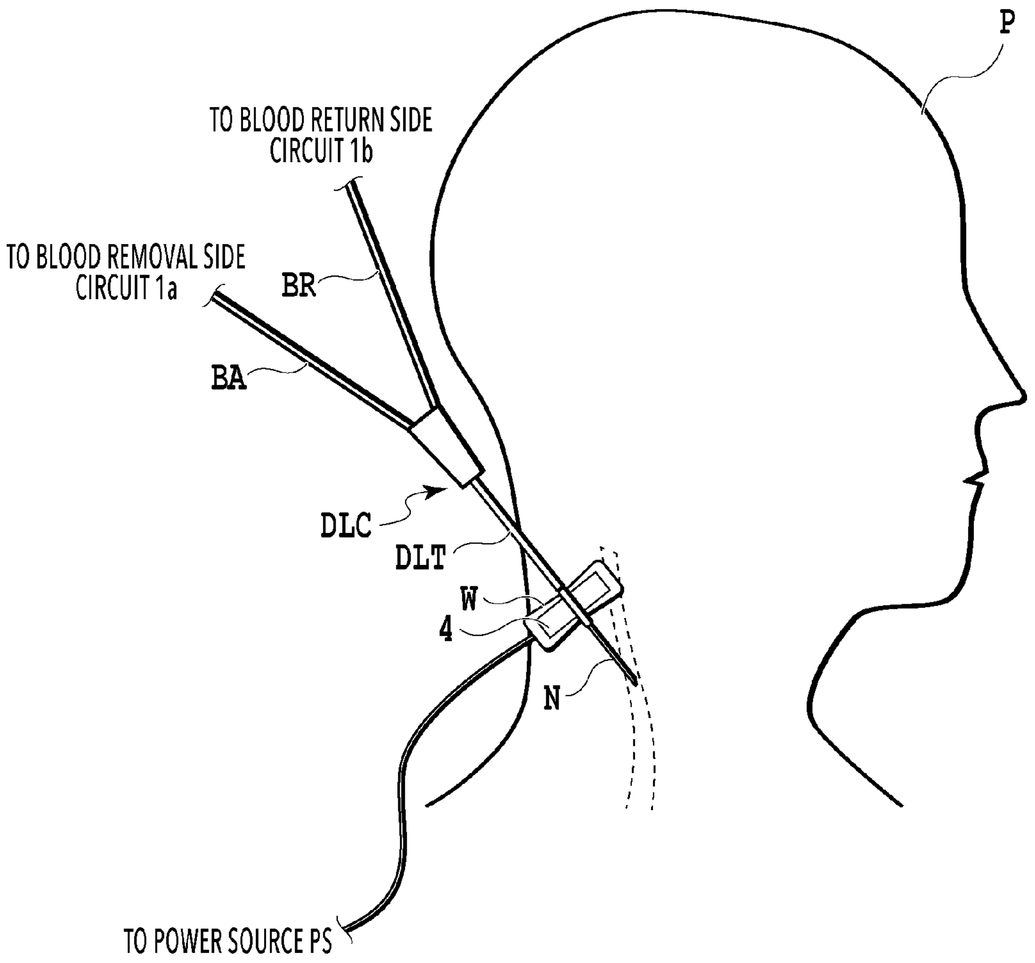
FIG. 14 is a diagram illustrating a configuration of a needle removal detector and a puncture needle according to a third embodiment.

FIG. 14 is a diagram illustrating the configurations of the needle removal detector 4 and a puncture needle N. As illustrated in FIG. 14, the puncture needle N is punctured into the neck of the patient P. The needle removal detector 4 is attached to the puncture needle N, and the needle removal detector 4 is coupled to the power source PS. The puncture needle N has a double-lumen structure (a double-lumen catheter DLC).

The double-lumen catheter DLC mainly includes the puncture needle N, a double-lumen tube DLT, a blood removal side bifurcation BA, and a blood return side bifurcation BR. The double-lumen catheter DLC has a structure in which the single puncture needle N bifurcates into the blood removal side circuit 1*a* and the blood return side circuit 1*b*. One end of the double-lumen tube DLT is coupled to the puncture needle N. The other end of the double-lumen tube DLT bifurcates into the blood removal side bifurcation BA and the blood return side bifurcation BR. The blood removal side bifurcation BA is coupled to the blood removal side circuit 1*a*, and the blood return side bifurcation BR is coupled to the blood return side circuit 1*b*. Note that, FIG. 14 illustrates a state of puncture into the neck; however, the puncture destination is not limited thereto, and the puncture needle N may be punctured into the thigh, under the collarbone, or the like.

The puncture needle N is formed integrally with a wing portion W. The needle removal detector 4 is provided to the wing portion W. The needle removal detector 4 is, for example, implemented as a touch sensor in the form of a sheet and is evaporated onto the wing portion W. In other words, the needle removal detector 4 is integral with the puncture needle N. The touch sensor may be a capacitive touch sensor, a resistive touch sensor, or the like. In a case where the needle removal detector 4 is implemented as the capacitive touch sensor, the power source PS applies the voltage to the electrode of the touch sensor while the puncture needle N is punctured into the patient P, and a change in a capacitance (a charge) generated with the needle being put in contact with the patient P is detected. In a case where the needle removal detector 4 is implemented as the resistive touch sensor, the power source PS applies the voltage to the electrode of the touch sensor while the puncture needle N is punctured into the patient P, and a change in a resistance value of a transparent conductive film generated with the needle being put in contact with the patient P is detected.

The needle removal detector 4 can detect whether the puncture needle N is punctured into the patient P by detecting the change in the capacitance or the change in the resistance value of the transparent conductive film by either of the above-described methods. In other words, the needle removal detector 4 can detect that the puncture needle N is removed from the patient P with the touch sensor detecting whether or not the puncture needle N is in contact with the body surface of the patient. Note that, the needle removal detector 4 transmits the above-described capacitance value or the resistance value to the controller C, and the controller C determines that the needle removal is carried out based on the change in the value. In this way, the needle removal detector 4 can detect that the needle removal is carried out also in a case where the puncture needle punctured into the patient P is a single needle such as the double-lumen catheter DLC.

The removal of the puncture needle N from the patient P is detected by the above-described configuration of the needle removal detector 4. The dialysate introduction stage end conditions and the blood return process end conditions in the third embodiment are similar to the conditions described in the first embodiment. Additionally, the processing of transition of the state mode regarding the blood pump P1 is also similar to the processing described in the first embodiment. Moreover, the blood return process described in the second embodiment may be applied to the third embodiment.

As above, the blood purification apparatus according to the third embodiment is described. In the third embodiment, it is also possible to prevent the drainage process and the like from being started while the puncture needle is left unremoved, and it is possible to detect the removal of the puncture needle also in a case where the puncture needle of the single needle such as the double-lumen catheter is used in the acute blood purification therapy.

The above-described embodiments are mere examples. The scope of the embodiments are not limited only to the described examples. Extra processing and/or constituents may be added to the above-described processing and constituents. Meanwhile, the above-described processing and constituents may be subjected to modifications without departing from the scope of the invention. Alternatively, a specific part of the above-described processing and constituents may be omitted. Moreover, the described order of processing may be changed.

Incidentally, the blood purification apparatus according to the embodiments is implemented by a computer program to be executed by the controller C. Here, the computer program may be stored in a non-transitory storage medium. Examples of the non-transitory storage medium include a read only memory (ROM), a random access memory (RAM), a register, a cache memory, a semiconductor memory apparatus, a magnetic medium such as a built-in hard disk drive and a removable disk drive, a magneto-optical medium, an optical medium such as a CD-ROM disc and a digital versatile disc (DVD), and so forth.

REFERENCE SIGNS LIST

1 blood circuit
1*a* blood removal side circuit
1*b* blood return side circuit
2 blood purifier
3 air introducer
3*a* air pump
3*b* air introduction route
3*c* on-off valve
3*d* air filter
3*e* air filter
3*f* on-off valve
4 needle removal detector
5 blood concentration detector
5*a* blood concentration detector
5*b* blood concentration detector
6 bubble detector
6*a* bubble detector
6*b* bubble detector
7*a* blood removal side air trap chamber
7*b* blood return side air trap chamber
100 blood purification apparatus
200 blood purification apparatus
IL dialysate introduction line
EL drainage line
PL priming liquid line
P1 blood pump
P2 dialysate pump
P3 drainage pump
P dialysate port
V1 to V6 on-off valve
EPa electrode
EPb electrode
EPc electrode
IA impedance adjustment circuit
A1 differential amplification circuit
A2 differential amplification circuit
R rectifier circuit
HF high cut filter
N puncture needle
W wing portion
RN blood removal side puncture needle AN blood return side puncture needle
DLC double-lumen catheter
DLT double-lumen tube
BA blood removal side bifurcation
BR blood return side bifurcation
C controller
PS power source

The invention claimed is:

1. A blood purification apparatus comprising:

a blood circuit which is coupled with a puncture needle punctured into a patient and through which blood from the patient flows;

a blood pump that is provided to the blood circuit and delivers liquid in the blood circuit by being driven;

a needle removal detector that detects removal of the puncture needle from the patient;

a controller that starts a blood return process to return the blood in the blood circuit to the patient and puts the blood pump in a non-active state in response to determination that the blood return process ends;

a dialysate introduction circuit that introduces dialysate into the blood circuit in the blood return process, the dialysate introduction circuit includes a priming liquid line that introduces the dialysate into the blood circuit and fills the blood circuit with the dialysate in a priming process carried out before the blood return process;

an air introducer that pushes out the dialysate introduced in the blood circuit by introducing air into the blood circuit in the blood return process;

a rehydration line coupled to the air introducer to introduce the air from the air introducer into the blood circuit through the rehydration line so that the dialysate is introduced into the blood circuit to rehydrate the blood;

wherein the controller determines whether to end a dialysate introduction stage to introduce the dialysate into the blood circuit based on an amount of returned blood and/or elapsed time, and starts an air introduction stage to introduce the air into the blood circuit in response to a determination that the dialysate introduction stage ends;

wherein the air introducer is coupled to the dialysate introduction circuit and introduces the air into the blood circuit through the dialysate introduction circuit;

wherein the air introducer further includes an on-off valve; and wherein the needle removal detector obtains a predetermined biological parameter by detecting a change in impedance based on an electric signal inputted from a differential amplification circuit.

2. The blood purification apparatus according to claim 1, wherein the controller puts the blood pump in an active state in response to detection of needle removal.

3. The blood purification apparatus according to claim 1, wherein the controller determines that the blood return process ends based on a returned blood flow rate and/or an elapsed time.

4. The blood purification apparatus according to claim 1, wherein the controller determines that the blood return process ends based on detection of no blood flowing in the blood circuit and/or detection of bubbles in the blood circuit.

5. The blood purification apparatus according to claim 1, wherein the air introducer is coupled to the blood circuit and introduces the air into the blood circuit.

6. The blood purification apparatus according to claim 5, further comprising:

a chamber that is provided to the blood circuit and stores the blood in the blood circuit, wherein the air introducer is coupled to the chamber and adjusts a liquid level in the chamber by feeding the chamber with the air in a treatment other than the blood return process.

7. The blood purification apparatus according to claim 5, further comprising:

a chamber that is provided to the blood circuit and stores the blood in the blood circuit, wherein the blood pump is coupled to the chamber and introduces the air into the chamber as the air introducer in the blood return process.

8. The blood purification apparatus according to claim 1, wherein the needle removal detector includes a touch sensor integrally formed with the puncture needle and detects the removal of the puncture needle with the touch sensor detecting whether or not the puncture needle is in contact with a body surface of the patient.

9. A method executed by a blood purification apparatus including a blood circuit which is coupled with a puncture needle punctured into a patient and through which blood from the patient flows, a blood pump that is provided to the blood circuit and delivers liquid in the blood circuit by being driven, a needle removal detector that detects removal of the puncture needle from the patient, a dialysate introduction circuit that introduces dialysate into the blood circuit in a blood return process, introducing the dialysate via a priming liquid line of the dialysate introduction circuit by filling the blood circuit with the dialysate in a priming process carried out before the blood return process;

an air introducer that pushes out the dialysate introduced in the blood circuit by introducing air into the blood circuit in the blood return process; and a rehydration line coupled to the air introducer to introduce air from the air introducer into the blood circuit through the rehydration line so that the dialysate is introduced into the blood circuit to rehydrate the blood, the method comprising steps of:

detecting removal of the puncture needle;

starting the blood return process to return the blood in the blood circuit to the patient;

determining whether to end a dialysate introduction stage to introduce the dialysate into the blood circuit based on an amount of returned blood and/or elapsed time;

starting an air introduction stage to introduce the air into the blood circuit in response to determination that the dialysate introduction stage ends; and putting the blood pump in a non-active state in response to determination that the blood return process ends, wherein the air introducer is coupled to the dialysate introduction circuit and introduces the air into the blood circuit through the dialysate introduction circuit;

wherein the air introducer further includes an on-off valve; and wherein the needle removal detector obtains a predetermined biological parameter by detecting a change in impedance based on an electric signal inputted from a differential amplification circuit.

10. The method according to claim 9, further comprising:

changing the blood pump to an active state, with a controller, in response to detection of needle removal.

11. The method according to claim 9, further comprising: determining, via a controller, that the blood return process ends based on a returned blood flow rate and/or an elapsed time.

* * * * *